United States Patent
Mueller et al.

(10) Patent No.: US 6,818,767 B2
(45) Date of Patent: Nov. 16, 2004

(54) QUINOLINE DERIVATIVES

(75) Inventors: Werner Mueller, Aesch (CH); Werner Neidhart, Hagenthal le Bas (FR); Philippe Pflieger, Schwoben (FR); Jean-Marc Plancher, Knoeringue (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 93 days.

(21) Appl. No.: 10/151,505

(22) Filed: May 20, 2002

(65) Prior Publication Data

US 2002/0198194 A1 Dec. 26, 2002

(30) Foreign Application Priority Data

May 21, 2001 (EP) ............................................. 01112370

(51) Int. Cl.[7] .................. C07D 215/42; C07D 409/04; C07D 239/84; A61P 3/00; A61K 31/517
(52) U.S. Cl. ........................ 544/128; 546/176; 546/179
(58) Field of Search ................................ 546/176, 179; 544/128

(56) References Cited

U.S. PATENT DOCUMENTS

| 3,272,824 A | 9/1966 | Ebetino et al. |
| 4,035,367 A | 7/1977 | Simpson |
| 4,598,089 A | 7/1986 | Hadvary et al. |
| 6,004,996 A | 12/1999 | Shah et al. |

FOREIGN PATENT DOCUMENTS

| EP | 185 359 | 6/1986 | |
| EP | 189 577 | 8/1986 | |
| EP | 443 429 | 8/1991 | |
| EP | 524 495 | 1/1993 | |
| EP | 0 882 717 | 12/1998 | |
| GB | 991 838 | 5/1965 | |
| WO | WO 99/34786 | 7/1999 | |
| WO | WO 00/09122 | 2/2000 | |
| WO | WO 00/09123 | 2/2000 | |
| WO | WO 02 20488 | 3/2002 | |
| WO | WO 200220488 A2 * | 3/2002 | ....... A61K/31/4706 |

OTHER PUBLICATIONS

Chem. Abstract XP002209016 & ZA 6706512A for Cronin, Timothy H.; Hess, Hans J.E., (1968).
Chem. Abstract XP001063055 for Gauthier B. et al., vol. 1, No. 44, pp. 55–64 (1986).
Negishi, E., Acc. Chem. Res., 15, pp. 340–348 (1982).
Buchwald et al., Acc. Chem. Res., 31, pp. 805–818 (1998).
Fu et al., J. Org. Chem., 64, pp. 10–11 (1999) with 9 pgs. of Supporting Information.
Buchwald et al., J. Am. Chem. Soc., 118, pp. 10333–10334 (1996) with 17 pgs. of Supporting Information.
Ragan et al., Synthesis, pp. 1599–1603 (1998).
Stille, J., Angew. Chem. Int. Ed. Engl., 25, pp. 508–524 (1986).
Rossi et al., Org. Prep. Proceed. Int., 27, pp. 127–160 (1995).
Deutsch et al., Synth. Commun., 21, pp. 505–513 (1991).

* cited by examiner

Primary Examiner—Richard L. Raymond
Assistant Examiner—Hong Liu
(74) Attorney, Agent, or Firm—George W. Johnston; John P. Parise

(57) ABSTRACT

Quinoline derivatives are useful as neuropeptide Y (NPY) receptor ligands and are particularly effective as neuropeptide Y (NPY) antagonists. These compounds are useful in pharmaceutical preparations for the treatment or prevention of arthritis, cardiovascular diseases, diabetes, renal failure, eating disorders, or obesity.

88 Claims, No Drawings

QUINOLINE DERIVATIVES

BACKGROUND OF THE INVENTION

The present invention is concerned with novel quinoline derivatives useful as neuropeptide Y (NPY) receptor ligands, particularly neuropeptide Y (NPY) antagonists.

SUMMARY OF THE INVENTION

The subject invention provides compounds of formula:

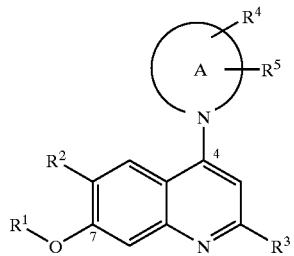

wherein:

$R^1$ is hydrogen, alkyl, alkoxyalkyl, alkenyl, alkinyl, hydroxyalkyl, aralkyl, heterocyclylalkyl, cycloalkylalkyl, $NH_2$—$SO_2$—, monoalkylamino-$SO_2$—, dialkylamino-$SO_2$—, alkyl-$SO_2$—, aryl, $NH_2$-alkyl, monoalkylaminoalkyl, dialkylaminoalkyl, alkoxycarbonylalkyl, carboxyalkyl, aryl-$SO_2$—O-alkyl, cycloalkyl, or cycloalkylalkyl;

$R^2$ is hydrogen, halogen, alkyl, alkenyl, alkinyl, aralkyl, heteroarylalkyl, hydroxyalkyl, alkoxy, alkoxyalkoxy, hydroxyalkoxyalkyl, aryloxy, arylamino, heteroarylamino, $NH_2$—, monoalkylamino, dialkylamino, heterocyclyl, arylalkylamino, heteroarylalkylamino, aryl, arylalkoxy, or heteroarylalkoxy;

$R^3$ is hydrogen, alkyl, $NH_2$—, monoalkylamino, dialkylamino, or alkoxy;

$R^4$ is hydrogen, alkyl, cycloalkyl, alkoxy, hydroxy, $NH_2$—, monoalkylamino, dialkylamino, acetylamino, cyano, hydroxyalkyl, alkoxyalkyl, cycloalkoxy, alkoxyalkoxy, cycloalkylalkoxy, heterocyclyl, heterocyclyloxy, heterocyclyloxyalkoxy, hydroxyalkoxy, alkoxycarbonyl, carboxy, heterocyclylalkyl, alkyl-$SO_2$—, or aryl-$SO_2$—;

$R^5$ is hydrogen, alkyl, cycloalkyl, alkoxy, hydroxy, $NH_2$—, monoalkylamino, dialkylamino, acetylamino, cyano, hydroxyalkyl, alkoxyalkyl, cycloalkoxy, alkoxyalkoxy, cycloalkylalkoxy, heterocyclyl, heterocyclyloxy, heterocyclyloxyalkoxy, hydroxyalkoxy, alkoxycarbonyl, carboxy, heterocyclylalkyl, alkyl-$SO_2$—, or aryl-$SO_2$—;

A is a 5- to 10-membered mono- or bicyclic saturated heterocyclic ring comprising the nitrogen atom which is attached to the quinoline ring or a 5- to 10-membered mono- or bicyclic saturated heterocyclic ring comprising the nitrogen atom which is attached to the quinoline ring, which is substituted by one or two further heteroatoms which are independently selected from the group consisting or oxygen, sulfur and nitrogen;

and pharmaceutically acceptable salts or esters thereof.

A preferred embodiment is where $R^1$ is hydrogen, alkyl, alkoxyalkyl, alkenyl, alkinyl, hydroxyalkyl, aralkyl, heterocyclylalkyl, cycloalkylalkyl, $NH_2$—$SO_2$—, monoalkylamino-$SO_2$—, dialkylamino-$SO_2$—, or alkyl-$SO_2$—; $R^4$ is hydrogen, alkyl, alkoxy, hydroxy, $NH_2$—, monoalkylamino, dialkylamino, acetylamino, or cyano; $R^5$ is hydrogen; and A is a saturated ring consisting of the nitrogen atom which is attached to the quinoline ring and a —$(CH_2)_n$— moiety with n being 4, 5, or 6. Preferred compounds are where $R^1$ is hydrogen, cycloalkylalkyl, aralkyl, or heteroarylalkyl. Further preferred compounds are where $R^1$ is hydrogen, aralkyl or heteroarylalkyl, favorably hydrogen, phenylalkyl, pyridinylalkyl, phenylalkyl wherein the phenyl cycle is substituted by one to three substituents independently selected from the group consisting of alkoxy, cyano and halogen, and pyridinylalkyl wherein the pyridinyl cycle is substituted by one to three substituents independently selected from the group consisting of alkoxy, cyano and halogen. Especially preferred is where $R^1$ is hydrogen, cyclopropylmethyl, (methoxyphenyl) methyl, (cyanophenyl) methyl, (chlorophenyl) methyl, pyridinylmethyl, chloropyridinylmethyl, or fluoropyridinylmethyl.

Favored groups of compounds are where $R^2$ is hydrogen, alkyl or halogen. Especially preferred is where $R^2$ is hydrogen, butyl, fluoro, chloro or bromo.

$R^3$ is favorably hydrogen, alkyl, or $NH_2$—. Methyl is a preferred alkyl group.

$R^4$ is favorably hydrogen, alkoxy, alkoxyalkyl, hydroxyalkyl or hydroxy. A is preferably a pyrrolidinyl or azepanyl ring, with the pyrrolidinyl ring being favored.

The subject invention also provides compounds of formula:

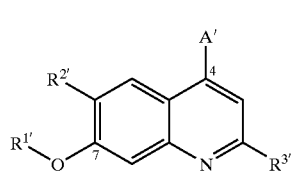

wherein:

$R^{1'}$ is hydrogen, phenylalkyl, pyridinylalkyl, phenylalkyl wherein the phenyl cycle is substituted by a substituent selected from the group consisting of alkoxy, cyano and halogen, and pyridinylalkyl wherein the pyridinyl cycle is substituted by a substituent selected from the group consisting of alkoxy, cyano and halogen;

$R^{2'}$ is is hydrogen, alkyl or halogen;

$R^{3'}$ is hydrogen or alkyl;

A' is selected from the group consisting of pyrrolidinyl, pyrrolidinyl substituted by hydroxy, alkyloxy, hydroxyalkyl or alkyloxyalkyl, and azepanyl;

and pharmaceutically acceptable salts and esters thereof.

Some favored compounds are where $R^{3'}$ is hydrogen or methyl, A' is pyrrolidinyl, $R^{2'}$ is alkyl, such as butyl, and $R^{1'}$ is hydrogen, e.g. 6-butyl-4-pyrrolidin-1-yl-quinolin-7-ol or a pharmaceutically acceptable salt or ester thereof $R^{1'}$ may also be (cyanophenyl)methyl, e.g. 4-(6-butyl-4-pyrrolidin-1-yl-quinolin-7-yloxymethyl)-benzonitrile or a pharmaceutically acceptable salt or ester thereof Other favored compounds are where $R^{3'}$ is methyl, A' is azepanyl, $R^{2'}$ is hydrogen, and $R^{1'}$ is pyridinylmethyl, e.g. 4-azepan-1-yl-2-methyl-7-(pyridin-4-ylmethoxy)-quinoline or a pharmaceutically acceptable salt or ester thereof. $R^{1'}$ may also be (cyanophenyl)methy, e.g. 4-(4-azepan-1-yl-2-methyl-quinolin-7-yloxymethyl)-benzonitrile or 3-(4-azepan-1-yl-2-methyl-quinolin-7-yloxymethyl)-benzonitrile or a pharmaceutically acceptable salts or esters thereof.

Preferred compounds include those where A' is pyrrolidinyl or pyrrolidinyl which is substituted by hydroxy, alkyloxy, hydroxyalkyl or alkyloxyalkyl. A favored group is where A' is pyrrolidinyl, $R^{2'}$ is hydrogen or halogen. $R^{1'}$ can favorably-be hydrogen, phenylalkyl wherein the phenyl cycle is substituted by a substituent selected from the group consisting of alkoxy, cyano and halogen, and pyridinylalkyl wherein the pyridinyl cycle is substituted by a substituent selected from the group consisting of alkoxy, cyano and halogen. When $R^{1'}$ is hydrogen, 2-methyl-4-pyrrolidin-1-yl-quinolin-7-ol or a pharmaceutically acceptable salt or ester thereof is favored. When $R^{1'}$ is (methoxyphenyl)methyl, 7-(3-methoxy-benzyloxy)-2-methyl-4-pyrrolidin-1-yl-quinoline and pharmaceutically acceptable salts and esters thereof is favored. When $R^{1'}$ is (cyanophenyl)methyl, 2-(2-methyl-4-pyrrolidin-1-yl-quinolin-7-yloxymethyl)-benzonitrile and 4-(2-methyl-4-pyrrolidin-1-yl-quinolin-7-yloxymethyl)-benzonitrile, as well as pharmaceutically acceptable salts and esters thereof are favored. Where $R^{1'}$ is (chlorophenyl)methyl, 7-(3-chloro-benzyloxy)-2-methyl-4-pyrrolidin-1-yl-quinoline and 7-(4-chloro-benzyloxy)-2-methyl-4-pyrrolidin-1-yl-quinoline, as well as pharmaceutically acceptable salts and esters thereof are preferred. $R^{1'}$ is (chloropyridinyl)methyl, 7-(2-chloro-pyridin-3-ylmethoxy)-2-methyl-4-pyrrolidin-1-yl-quinoline and pharmaceutically acceptable salts and esters thereof are favored. When $R^{2'}$ is halogen, such as fluoro, and $R^{1'}$ is (cyanophenyl)methyl, the comopund 4-(6-fluoro-2-methyl-4-pyrrolidin-1-yl-quinolin-7-yloxymethyl)benzonitrile and pharmaceutically acceptable salts and esters thereof are preferred. Likewise, when $R^{1'}$ is (fluoropyridinyl)methyl, 6-fluoro-7-(2-fluoro-pyridin-3-ylmethoxy)-2-methyl-4-pyrrolidin-1-yl-quinoline and pharmaceutically acceptable salts and esters thereof are preferred and when R' is (chloropyridinyl)methyl, 7-(2-chloro-pyridin-3-ylmethoxy)-6-fluoro-2-methyl-4-pyrrolidin-1-yl-quinoline and pharmaceutically acceptable salts and esters thereof are preferred.

Preferred compounds also include those where A' is pyrrolidinyl which is substituted by hydroxy, alkyloxy, hydroxyalkyl or alkyloxyalkyl. When A' is pyrrolidinyl which is substituted by hydroxy, $R^{1'}$ is (cyanophenyl)methyl, and $R^{2'}$ is hydrogen, the compounds (S) and (R)-4-[4-(3-hydroxy-pyrrolidin-1-yl)-2-methyl-quinolin-7-yloxymethyl]-benzonitrile and pharmaceutically acceptable salts and esters thereof are favored. When A' is pyrrolidinyl which is substituted by alkyloxy, such as methoxy, and $R^{1'}$ is (cyanophenyl)methyl, the compound (S)-4-[4-(3-methoxy-pyrrolidin-1-yl)-2-methyl-quinolin-7-yloxymethyl]-benzonitrile and pharmaceutically acceptable salts and esters thereof are preferred. If A' is pyrrolidinyl which is substituted by ethoxy, $R^{2'}$ is hydrogen, and $R^{1'}$ is (cyanophenyl)methyl, then (S)-4-[4-(3-ethoxy-pyrrolidin-1-yl)-2-methyl-quinolin-7-yloxymethyl]-benzonitrile or a pharmaceutically acceptable salt or ester thereof is favored. If $R^{1'}$ is (fluoropyridinyl)methyl, then (S) 4-(3-ethoxy-pyrrolidin-1-yl)-7-(2-fluoro-pyridin-3-ylmethoxy)-2-methyl-quinoline or a pharmaceutically acceptable salt or ester thereof is favored. If $R^{1'}$ is (chloropyridinyl)methyl, then (S) 7-(2-chloro-pyridin-3-ylmethoxy)-4-(3-ethoxy-pyrrolidin-1-yl)-2-methyl-quinoline or a pharmaceutically acceptable salt or ester thereof is favored.

When A' is pyrrolidinyl which is substituted by hydroxyalkyl, e.g. hydroxymethyl, $R^{2'}$ is hydrogen, and $R^{1'}$ is (fluoropyridinyl)methyl, then (S)-{1-[7-(2-fluoro-pyridin-3-ylmethoxy)-2-methyl-quinolin-4-yl]-pyrrolidin-2-yl}-methanol or a pharmaceutically acceptable salt or ester thereof is the favored compound. If $R^{1'}$ is (chloropyridinyl) methyl, then the preferred compound is (S)-{1-[7-(2-chloro-pyridin-3-ylmethoxy)-2-methyl-quinolin-4-yl]-pyrrolidin-2-yl}-methanol or a pharmaceutically acceptable salt or ester thereof, and if $R^{1'}$ is (cyanophenyl)methy, then the preferred compound is (S) or (R)-4-[4-(2-hydroxymethyl-pyrrolidin-1-yl)-2-methyl-quinolin-7-yloxymethyl]-benzonitrile or a pharmaceutically acceptable salt or ester thereof.

Other favored compounds are where $R^{2'}$ is halogen, e.g. fluoro, and $R^{1'}$ is (cyanophenyl)methyl, for example (S)-4-[6-fluoro-4-(2-hydroxymethyl-pyrrolidin-1-yl)-2-methyl-quinolin-7-yloxymethyl]-benzonitrile or a pharmaceutically acceptable salt or ester thereof. If A' is pyrrolidinyl which is substituted by alkyloxyalkyl, such as methoxymethyl, and $R^{2'}$ is hydrogen, and $R^{1'}$ is (fluoropyridinyl)methyl, then the favored compound is (S)-7-(2-fluoro-pyridin-3-ylmethoxy)-4-(2-methoxymethyl-pyrrolidin-1-yl)-2-methyl-quinoline or a pharmaceutically acceptable salt or ester thereof. Should $R^{1'}$ be (chloropyridinyl)methyl, then (S)-7-(2-chloro-pyridin-3-ylmethoxy)-4-(2-methoxymethyl-pyrrolidin-1-yl)-2-methyl-quinoline or a pharmaceutically acceptable salt or ester thereof would be the favored compound.

For brevity, each and every combination of substituents has not been listed individually. However, it is intended that each and every combination of substituents be considered described and enabled by the present specification.

DETAILED DESCRIPTION OF THE PREFERRED EMBODIMENTS

The subject invention will be described in terms of its preferred embodiments that are set forth to aid in understanding the invention. While illustrative of the invention, these embodiments are not to be construed as limiting.

The invention is concerned especially with compounds of formula I

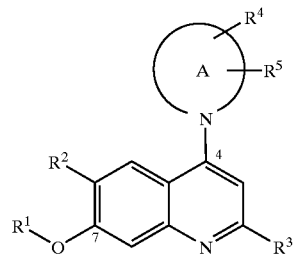

and pharmaceutically acceptable salts and esters thereof, wherein $R^1$ is hydrogen, alkyl, alkoxyalkyl, alkenyl, alkinyl, hydroxyalkyl, aralkyl, heterocyclylalkyl, cycloalkylalkyl, $NH_2$—$SO_2$—, monoalkylamino-$SO_2$—, dialkylamino-$SO_2$—, alkyl-$SO_2$—, aryl, $NH_2$-alkyl, monoalkylaminoalkyl, dialkylaminoalkyl, alkoxycarbonylalkyl, carboxyalkyl, aryl-$SO_2$—O-alkyl, cycloalkyl or cycloalkylalkyl;

$R^2$ is hydrogen, halogen, alkyl, alkenyl, alkinyl, aralkyl, heteroarylalkyl, hydroxyalkyl, alkoxy, alkoxyalkoxy, hydroxyalkoxyalkyl, aryloxy, arylamino, heteroarylamino, $NH_2$—, monoalkylamino, dialkylamino, heterocyclyl, arylalkylamino, heteroarylalkylamino, aryl, arylalkoxy or heteroarylalkoxy;

$R^3$ is hydrogen, alkyl, $NH_2$—, monoalkylamino, dialkylamino or alkoxy;

$R^4$ is hydrogen, alkyl, cycloalkyl, alkoxy, hydroxy, $NH_2$—, monoalkylamino, dialkylamino, acetylamino, cyano, hydroxyalkyl, alkoxyalkyl, cycloalkoxy, alkoxyalkoxy, cycloalkylalkoxy, heterocyclyl, heterocyclyloxy, heterocyclyloxyalkoxy, hydroxyalkoxy, alkoxycarbonyl, carboxy, heterocyclylalkyl, alkyl-$SO_2$— or aryl-$SO_2$—;

$R^5$ is hydrogen, alkyl, cycloalkyl, alkoxy, hydroxy, $NH_2$—, monoalkylamino, dialkylamino, acetylamino, cyano, hydroxyalkyl, alkoxyalkyl, cycloalkoxy, alkoxyalkoxy, cycloalkylalkoxy, heterocyclyl, heterocyclyloxy, heterocyclyloxyalkoxy, hydroxyalkoxy, alkoxycarbonyl, carboxy, heterocyclylalkyl, alkyl-$SO_2$— or aryl-$SO_2$—; and A is a 5- to 10-membered mono- or bicyclic saturated heterocyclic ring comprising the nitrogen atom which is attached to the quinoline ring and optionally one or two further heteroatoms which are independently selected from oxygen, sulfur and nitrogen.

The compounds of formula I and their pharmaceutically usable salts and are novel and have valuable pharmacological properties. They are neuropeptide ligands, for example neuropeptide receptor antagonists and in particular, they are selective neuropeptides Y Y5 receptor antagonists.

Neuropetide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonise neuropeptide Y at the Y5 receptor subtype represent an approach to the treatment of eating disorders such as obesity and hyperphagia.

The current approach is aiming at medical intervention to induce weight loss or prevention of weight gain. This is achieved by interfering with appetite control, which is mediated by the Hypothalamus, an important brain region proven to control food intake. Herein, neuropeptide Y (NPY) has been proven to be one of the strongest central mediators of food intake in several animal species. Increased NPY levels result in profound food intake. Various receptors of neuropeptide Y (NPY) have been described to play a role in appetite control and weight gain. Interference with these receptors is likely to reduce appetite and consequently weight gain. Reduction and long-term maintenance of body weight can also have beneficial consequences on con associated risk factors such as arthritis, cardiovascular diseases, diabetes and renal failure.

Accordingly, the compounds of formula I can be used in the prophylaxis or treatment of of arthritis, cardiovascular diseases, diabetes, renal failure and particularly eating disorders and obesity.

The subject invention provides compounds of formula I and their salts and esters, the use of such compounds as therapeutically active substances, a process for the manufacture of such compounds, intermediates, pharmaceutical compositions, medicaments containing such compounds, and their pharmaceutically usable salts and esters. The use of the compounds, esters and salts for the prophylaxis and/or therapy of illnesses, especially in the treatment or prophylaxis of arthritis, cardiovascular diseases, diabetes, renal failure and particularly eating disorders such as hyperphagia and particularly obesity, is also provided. In addition the invention includes the use of the compounds, salts and esters for the production of medicaments for the treatment or prophylaxis of arthritis, cardiovascular diseases, diabetes, renal failure and particularly eating disorders and obesity.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, 2-hydroxyethoxy, 2-methoxyethoxypreferably methoxy and ethoxy and most preferred methoxy.

The term "aryloxy", alone or in combination, signifies a group of the formula aryl-O— in which the term "aryl" has the previously given significance, such as phenyloxy.

The term "aryl", alone or in combination, signifies a phenyl or naphthyl group, preferably a phenyl group which optionally carries one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro and the like, such as phenyl, chlorophenyl, trifluoromethylphenyl, chlorofluorophenyl, aminophenyl, methylcarbonylphenyl, methoxyphenyl, methylendioxyphenyl, 1-naphthyl and 2-naphthyl.

Preferred is phenyl, 3-chlorophenyl, 3-trifluoromethylphenyl, 3-aminophenyl, 4-methylcarbonylphenyl, 4-methoxyphenyl and particularly phenyl.

The term "aralkyl", alone or in combination, signifies an alkyl or cycloalkyl group as previously defined in which one hydrogen atom has been replaced by an aryl group as previously defined. Preferred are benzyl, benzyl substituted with hydroxy, alkoxy or halogen, preferably fluorine. Particularly preferred is benzyl.

The term "heterocyclyl", alone or in combination, signifies a saturated, partially unsaturated or aromatic 4- to 10-membered heterocycle which contains one or more, preferably one ore two hetero atoms selected from nitrogen, oxygen and sulfur, wherein oxygen and particularly nitrogen are preferred. If desired, it can be substituted on one or more carbon atoms by halogen, alkyl, alkoxy, oxo, cyano, haloalkyl preferably trifluoromethyl and heterocyclyl, preferably morpholinyl and pyrrolidinyl, and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. The term "heterocyclyl" also includes the term heteroaryl. Examples of heterocyclyl groups are pyridinyl, pyrrolidinyl, piperidinyl, morpholinyl, piperazinyl, 3,4-dihydro-1H-isoquinolinyl, azepanyl, tetrahydrofuranyl and thiophenyl, wherein each of these rings can be substituted by one or more, preferably one or two substituents independently selected from alkyl, alkoxy, halogen, trifluoromethyl, cyano, morpholinyl and pyrrolidinyl. Particularly preferred examples of heterocycly are pyridinyl, pyrrolidinyl, piperidinyl, morpholinyl, thiophenyl, tetrahydrofuranyl and furyl, wherein each of these rings is optionally substituted with one or more, preferably one or two substituents selected from alkyl, alkoxy, halogen, trifluoromethyl, cyano, morpholinyl and pyrrolidinyl.

The term "heteroaryl", alone or in combination, signifies aromatic 5- to 10-membered heterocycle which contains one or more, preferably one or two hetero atoms selected from nitrogen, oxygen and sulfur, wherein nitrogen or oxygen are preferred. If desired, it can be substituted on one or more carbon atoms by halogen, alkyl, alkoxy, cyano, haloalkyl, heterocyclyl, preferably trifluoromethyl. Preferred heteroaryl cycles are pyridinyl or thiophenyl optionaly substituted by one or more, preferably one or two substituents independently selected from halogen, alkyl, alkoxy, cyano, haloalkyl, preferably trifluoromethyl, and heterocyclyl, preferably morpholinyl or pyrrolidinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —NH$_2$, methylamino, ethylamino, dimethylamino, diethylamino, methylethylamino, pyrrolidin-1-yl or piperidino etc., preferably amino, dimethylamino and diethylamino and particularly primary amino.

The term "halogen" signifies fluorine, chlorine, bromine or iodine and preferably fluorine, chlorine or bromine.

The term "alkenyl", alone or in combination signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl.

The term "alkinyl", alone or in combination signifies a straight-chain or branched hydrocarbon residue comprising a carbon carbon triple bond and up to 8, preferably up to 6, particularly preferred up to 4 carbon atoms. Examples of alkinyl groups are ethinyl, 1-propinyl, 2-propinyl, 1-butinyl, 2-butinyl and 3-butinyl.

The term "carboxy", alone or in combination signifies the —COOH group.

The term "carboxyalkyl", alone or in combination signifies an alkyl group as defined before, wherein one or more, preferably one hydrogen atom is replaced by a carboxy group. An example is carboxymethyl.

The term "hydroxyalkyl", alone or in combination signifies an alkyl group as define before, wherein one or more, preferably one hydrogen atom is replaced by a hydroxy group.

The term "aryloxy", alone or in combination signifies the group aryl-O—, wherein the term aryl is defined as before.

The term "cyano", alone or in combination signifies the group —CN.

The term "heterocyclyloxy", alone or in combination signifies the group heterocyclyl-O—, wherein the term heterocyclyl is defined as before.

The term "actetylamino", alone or in combination signifies the group —NH—CO—CH$_3$.

The term "arylamino", alone or in combination signifies the group aryl-NH— or

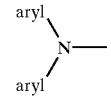

wherein the term aryl is defined as before and, wherein both aryl groups are the same or are different.

The term "heteroarylamino", alone or in combination signifies the group heteroaryl-NH— or

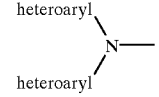

wherein the term heteroaryl is defined as before and, wherein both heteroaryl groups are the same or are different.

The term "pharmaceutically acceptable salts" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically usable solvates.

"Pharmaceutically acceptable esters" means that compounds of formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of formula (I), similar to the metabolically labile esters, which are capable of producing the parent compounds of formula (I) in vivo, are within the scope of this invention.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123.

Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragees and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

In the nomenclature used in the present description the ring atoms of the quinoline ring are numbered as follows:

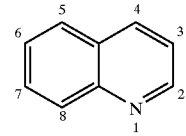

Preferred are compounds of the formula I, wherein $R^1$ is hydrogen, alkyl, alkoxyalkyl, alkenyl, alkinyl, hydroxyalkyl, aralkyl, heterocyclylalkyl, cycloalkylalkyl, $NH_2$—$SO_2$—, monoalkylamino-$SO_2$—, dialkylamino-$SO_2$— or alkyl-$SO_2$—;

$R^2$ is hydrogen, halogen, alkyl, alkenyl, alkinyl, aralkyl, heteroarylalkyl, hydroxyalkyl, alkoxy, alkoxyalkoxy, hydroxyalkoxyalkyl, aryloxy, arylamino, heteroarylamino, $NH_2$—, mono- or dialkylamino, heterocyclyl, arylalkylamino, heteroarylalkylamino, aryl, heteroaryl, arylalkoxy or heteroarylalkoxy;

$R^3$ is hydrogen, alkyl, $NH_2$—, monoalkylamino, dialkylamino or alkoxy;

$R^4$ is hydrogen, alkyl, alkoxy, hydroxy, $NH_2$—, monoalkylamino, dialkylamino, acetylamino or cyano;

$R^5$ is hydrogen;

A is a saturated ring consisting of a nitrogen atom which is attched to the quinoline ring and a —$(CH_2)_n$— moiety with n being 4, 5, or 6;

and pharmaceutically acceptable salts and esters thereof.

Preferred compounds of formula I are those, wherein $R^1$ is hydrogen, alkyl, alkenyl, hydroxyalkyl, aralkyl, heterocyclylalkyl, cycloalkylalkyl, dialkylamino-$SO_2$—, alkyl-$SO_2$—, dialkylaminoalkyl, alkoxycarbonylalkyl, aryl-$SO_2$—O-alkyl or cycloalkylalkyl.

In a further preferred embodiment of the invention $R^1$ is hydrogen, alkyl, alkoxyalkyl, alkenyl, alkinyl, hydroxyalkyl, aralkyl, heterocyclylalkyl, cycloalkylalkyl, $NH_2$—, mono- or dialkylamino-$SO_2$—, or alkyl-$SO_2$—. A further preferred embodiment of the present invention $R^1$ is hydrogen, cycloalkylalkyl, aralkyl, or heteroarylalkyl. Further preferred are compounds according to formula (I), wherein $R^1$ is hydrogen, aralkyl or heteroarylalkyl. Particularly preferred are compounds of formula (I), wherein $R^1$ is hydrogen, phenylalkyl or pyridinylalkyl wherein the phenyl- and the pyridinyl cyles are optionally substituted with one to three substituents independently selected from the group consisting of alkyl, alkoxy, cyano, or halogen, preferably, methyl, alkoxy, cyano, or halogen. Further particularly preferred are compounds, wherein $R^1$ is hydrogen, cyclopropylmethyl, (methoxyphenyl)methyl, (cyanophenyl)methyl, (chlorophenyl)methyl, pyridinylmethyl, (fluropyridinyl)methyl, (chloropyridinyl)methyl, or (methylpyridinyl)methyl. Very preferred are compounds, wherein $R^1$ is hydrogen, cyclopropylmethyl, (methoxyphenyl)methyl, (cyanophenyl)methyl, (chlorophenyl)methyl or pyridinylmethyl. Particularly preferred are compounds of formula I, wherein $R^1$ is hydrogen, cyclopropylmethyl, (methoxyphenyl)methyl, (cyanophenyl)methyl, (chlorophenyl)methyl, pyridinylmethyl, chloropyridinylmethyl or fluoropyridinylmethyl.

In a preferred embodiment of the present invention $R^2$ is hydrogen, halogen, alkyl, alkenyl, alkinyl, aralkyl, heteroarylalkyl, hydroxyalkyl, alkoxy, alkoxyalkoxy, hydroxyalkoxyalkyl, aryloxy, arylamino, heteroarylamino, $NH_2$—, mono- or dialkylamino or aryl(alkyl)amino. In another preferred embodiment of the invention $R^2$ is hydrogen, alkyl, or halogen. Particularly preferred are compounds of formula (I), wherein $R^2$ is hydrogen. Likewise preferred are compounds according to formula (I), wherein $R^2$ is alkyl. Other preferred compounds of formula (I) are those, wherein $R^2$ is hydrogen, butyl, fluoro, chloro or bromo. Particularly preferred are hydrogen, butyl, fluoro or bromo.

A preferred aspect of the present invention are compounds according to formula I, wherein $R^3$ is hydrogen, alkyl, aralkoxy, heteroarylalkoxy, $NH_2$—, mono- or di-alkylamino. Further preferred compounds of formula (I) are those, wherein $R^3$ is hydrogen, alkyl, or $NH_2$—. Preferred compounds are those, wherein $R^3$ is alkyl, particularly methyl.

Preferred are compounds of formula I, wherein $R^4$ is hydrogen, alkyl, cycloalkyl, alkoxy, hydroxy, monoalkylamino, dialkylamino, hydroxyalkyl, alkoxyalkyl, cycloalkoxy, alkoxyalkoxy, cycloalkylalkoxy, heterocyclyl, heterocyclyloxyalkoxy, hydroxyalkoxy, alkoxycarbonyl, heterocyclylalkyl or alkyl-$SO_2$—.

In a preferred embodiment of the invention $R^4$ is hydrogen, alkyl or alkoxy. Another preferred aspect of the present invention are compounds of formula (I), wherein $R^4$ is hydrogen or alkoxy. Particularly preferred compounds of formula I are those, wherein $R^4$ is hydrogen, alkoxy, alkoxyalkyl, hydroxyalkyl or hydroxy. Very preferred is hydrogen.

Further preferred are those compounds of formula I, wherein A is a 5- to 10-membered mono- or bicyclic saturated heterocyclic ring comprising the nitrogen atom which is attached to the quinoline ring and optionally one or two further oxygen atoms. Preferred compounds according to formula I are those, wherein A is pyrrolidinyl, azepanyl, morpholinyl, 1,4-dioxa-8-aza-spiro(4.5)dec-8-yl or piperidinyl.

Other preferred compounds of formula (I) are those, wherein A is a pyrrolidinyl or azepanyl ring. Particularly preferred is a pyrrolidinyl ring.

Preferred compounds of formula I are those, wherein $R^5$ is hydrogen.

Examples of preferred compounds of formula (I) are 1. 7-Benzyloxy-2-methyl-4-pyrrolidin-1-yl-quinoline;
2. 2-Methyl-4-pyrrolidin-1-yl-quinolin-7-ol;
3. Dimethyl-sulfamic acid 2-methyl-4-pyrrolidin-1-yl-quinolin-7-yl ester;
4. Methanesulfonic acid 2-methyl-4-pyrrolidin-1-yl-quinolin-7-yl ester;
5. 7-Cyclopropylmethoxy-2-methyl-4-pyrrolidin-1-yl-quinoline;
6. 7-(3-Methoxy-benzyloxy)-2-methyl-4-pyrrolidin-1-yl-quinoline;
7. 7-Methoxy-2-methyl-4-pyrrolidin-1-yl-quinoline;
8. 2-Methyl-7-(pyridin-2-ylmethoxy)-4-pyrrolidin-1-yl-quinoline;
9. 7-Allyloxy-2-methyl-4-pyrrolidin-1-yl-quinoline;
10. 7-Isobutoxy-2-methyl-4-pyrrolidin-1-yl-quinoline;
11. 7-(2-Methoxy-benzyloxy)-2-methyl-4-pyrrolidin-1-yl-quinoline;
12. 2-Methyl-4-pyrrolidin-1-yl-7-(tetrahydro-furan-2-ylmethoxy)-quinoline;
13. 7-(4-Methoxy-benzyloxy)-2-methyl-4-pyrrolidin-1-yl-quinoline;
14. 2-(2-Methyl-4-pyrrolidin-1-yl-quinolin-7-yloxymethyl)-benzonitrile;
15. 4-(2-Methyl-4-pyrrolidin-1-yl-quinolin-7-yloxymethyl)-benzonitrile;
16. 2-Methyl-4-pyrrolidin-1-yl-7-(2-trifluoromethyl-benzyloxy)-quinoline;
17. 2-Methyl-4-pyrrolidin-1-yl-7-(3-trifluoromethyl-benzyloxy)-quinoline;
18. 2-Methyl-4-pyrrolidin-1-yl-7-(4-trifluoromethyl-benzyloxy)-quinoline;
19. 7-(2-Chloro-benzyloxy)-2-methyl-4-pyrrolidin-1-yl-quinoline;
20. 7-(3-Chloro-benzyloxy)-2-methyl-4-pyrrolidin-1-yl-quinoline;
21. 7-(4-Chloro-benzyloxy)-2-methyl-4-pyrrolidin-1-yl-quinoline;
22. 2-Methyl-7-(pyridin-3-ylmethoxy)-4-pyrrolidin-1-yl-quinoline;
23. 3-(2-Methyl-4-pyrrolidin-1-yl-quinolin-7-yloxymethyl)-benzonitrile;
24. 7-Isopropoxy-2-methyl-4-pyrrolidin-1-yl-quinoline;
25. 7-(2-Methoxy-ethoxy)-2-methyl-4-pyrrolidin-1-yl-quinoline;
26. 2-Methyl-7-(2-morpholin-4-yl-ethoxy)-4-pyrrolidin-1-yl-quinoline;
27. 2-Methyl-7-(pyridin-4-ylmethoxy)-4-pyrrolidin-1-yl-quinoline;
28. (S)-'7-Benzyloxy-4-(3-ethoxy-pyrrolidin-1-yl)-2-methyl-quinoline;
29. (S)-4-(3-Ethoxy-pyrrolidin-1-yl)-2-methyl-quinolin-7-ol;
30. (S)-4-(3-Ethoxy-pyrrolidin-1-yl)-7-(3-methoxy-benzyloxy)-2-methyl-quinoline;
31. (S)-4-[4-(3-Ethoxy-pyrrolidin-1-yl)-2-methyl-quinolin-7-yloxymethyl]-benzonitrile;
32. (S)-2-[4-(3-Ethoxy-pyrrolidin-1-yl)-2-methyl-quinolin-7-yloxymethyl]-benzonitrile;
33. 7-Benzyloxy-6-butyl-4-pyrrolidin-1-yl-quinoline;
34. 6-Butyl-4-pyrrolidin-1-yl-quinolin-7-ol;
35. 6-Butyl-7-methoxy-4-pyrrolidin-1-yl-quinoline;
36. 6-Butyl-7-ethoxy-4-pyrrolidin-1-yl-quinoline;
37. 6-Butyl-7-cyclopropylmethoxy-4-pyrrolidin-1-yl-quinoline;
38. 4-(6-Butyl-4-pyrrolidin-1-yl-quinolin-7-yloxymethyl)-benzonitrile;
39. 4-Azepan-1-yl-7-benzyloxy-2-methyl-quinoline;
40. 4-Azepan-1-yl-2-methyl-quinolin-7-ol;
41. 4-Azepan-1-yl-2-methyl-7-(pyridin-4-ylmethoxy)-quinoline;
42. 4-(4-Azepan-1-yl-2-methyl-quinolin-7-yloxymethyl)-benzonitrile;
43. 3-(4-Azepan-1-yl-2-methyl-quinolin-7-yloxymethyl)-benzonitrile;
44. 4-Azepan-1-yl-2-methyl-7-(pyridin-2-ylmethoxy)-quinoline;
45. 6-Bromo-7-methoxy-2-methyl-4-pyrrolidin-1-yl-quinoline;
46. 6-Bromo-2-methyl-4-pyrrolidin-1-yl-quinolin-7-ol;
47. 4-(6-Bromo-2-methyl-4-pyrrolidin-1-yl-quinolin-7-yloxymethyl)-benzonitrile;
48. 7-Methoxy-4-pyrrolidin-1-yl-quinolin-2-ylamine;
49. 7-Methoxy-4-pyrrolidin-1-yl-quinoline;
50. 4-Pyrrolidin-1-yl-quinolin-7-ol;
51. 7-(3,5-dimethoxy-benzyloxy)-2-methyl-4-pyrrolidin-1-yl-quinoline;
52. 7-(3,4-dimethoxy-benzyloxy)-2-methyl-4-pyrrolidin-1-yl-quinoline;

53. 7-ethoxy-2-methyl-4-pyrrolidin-1-yl-quinoline;
54. 2-Methyl-7-(6-methyl-pyridin-3-ylmethoxy)-4-pyrrolidin-1-yl-quinoline;
55. 2-methyl-7-(2-methyl-pyridin-3-ylmethoxy)-4-pyrrolidin-1-yl-quinoline;
56. 7-(6-chloro-pyridin-3-ylmethoxy)-2-methyl-4-pyrrolidin-1-yl-quinoline;
57. 7-(2-chloro-pyridin-3-ylmethoxy)-2-methyl-4-pyrrolidin-1-yl-quinoline;
58. 7-(2-fluoro-pyridin-3-ylmethoxy)-2-methyl-4-pyrrolidin-1-yl-quinoline;
59. 7-(2-chloro-6-methyl-pyridin-3-ylmethoxy)-2-methyl-4-pyrrolidin-1-yl-quinoline;
60. 7-(2-chloro-6-trifluoromethyl-pyridin-3-ylmethoxy)-2-methyl-4-pyrrolidin-1-yl-quinoline;
61. 5-(2-methyl-4-pyrrolidin-1-yl-quinolin-7-yloxymethyl)-pyridine-2-carbonitrile;
62. 7-(5-chloro-thiophen-2-ylmethoxy)-2-methyl-4-pyrrolidin-1-yl-quinoline;
63. 2-methyl-4-pyrrolidin-1-yl-7-(thiophen-3-ylmethoxy)-quinoline;
64. 4-(2-methyl-4-pyrrolidin-1-yl-quinolin-7-yloxy)-benzonitrile;
65. (S) 4-(3-ethoxy-pyrrolidin-1-yl)-7-(2-fluoro-pyridin-3-ylmethoxy)-2-methyl-quinoline;
66. (S) 7-(2-chloro-pyridin-3-ylmethoxy)-4-(3-ethoxy-pyrrolidin-1-yl)-2-methyl-quinoline;
67. (S) 4-(3-ethoxy-pyrrolidin-1-yl)-2-methyl-7-(pyridin-3-ylmethoxy)-quinoline;
68. (S) 5-[4-(3-ethoxy-pyrrolidin-1-yl)-2-methyl-quinolin-7-yloxymethyl]-pyridine-2-carbonitrile;
69. 4-azepan-1-yl-7-(3-methoxy-benzyloxy)-2-methyl-quinoline;
70. 2-(4-azepan-1-yl-2-methyl-quinolin-7-yloxy-methyl)-benzonitrile;
71. 4-azepan-1-yl-7-(3-chloro-benzyloxy)-2-methyl-quinoline;
72. 4-Azepan-1-yl-7-(4-chloro-benzyloxy)-2-methyl-quinoline;
73. 2-methyl-7-(6-morpholin-4-yl-pyridin-3-ylmethoxy)-4-pyrrolidin-1-yl-quinoline;
74. 2-methyl-4-pyrrolidin-1-yl-7-(6-pyrrolidin-1-yl-pyridin-3-ylmethoxy)-quinoline;
75. [2,2-dimethyl-3-(2-methyl-4-pyrrolidin-1-yl-quinolin-7-yloxy)-propyl]-dimethyl-amine;
76. 2-methyl-7-(1-methyl-piperidin-4-yloxy)-4-pyrrolidin-1-yl-quinoline;
77. 2-methyl-4-pyrrolidin-1-yl-7-(tetrahydro-furan-3-yloxy)-quinoline;
78. 2-Methyl-7-(1-methyl-piperidin-4-ylmethoxy)-4-pyrrolidin-1-yl-quinoline;
79. 2-methyl-7-(3-morpholin-4-yl-propoxy)-4-pyrrolidin-1-yl-quinoline;
80. (2-methyl-4-pyrrolidin-1-yl-quinolin-7-yloxy)-acetic acid ethyl ester;
81. 2-(2-methyl-4-pyrrolidin-1-yl-quinolin-7-yloxy)-ethanol;
82. oluene-4-sulfonic acid 2-(2-methyl-4-pyrrolidin-1-yl-quinolin-7-yloxy)-ethyl ester;
83. 2-methyl-7-(3-pyridin-2-yl-propoxy)-4-pyrrolidin-1-yl-quinoline;
84. 7-benzyloxy-2-methyl-4-morpholin-4-yl-quinoline;
85. (S)-1-(7-benzyloxy-2-methyl-quinolin-4-yl)-pyrrolidin-3-ol;
86. (R)-1-(7-benzyloxy-2-methyl-quinolin-4-yl)-pyrrolidin-3-ol;
87. (S)-[1-(7-benzyloxy-2-methyl-quinolin-4-yl)-pyrrolidin-2-yl]-methanol;
88. (S)-7-benzyloxy-4-(2-methoxymethyl-pyrrolidin-1-yl)-2-methyl-quinoline;
89. (S)-4-(2-Methoxymethyl-pyrrolidin-1-yl)-2-methyl-quinolin-7-ol;
90. (S)-7-(2-chloro-pyridin-3-ylmethoxy)-4-(2-methoxymethyl-pyrrolidin-1-yl)-2-methyl-quinoline;
91. (S)-7-(2-fluoro-pyridin-3-ylmethoxy)-4-(2-methoxymethyl-pyrrolidin-1-yl)-2-methyl-quinoline;
92. (S)-7-cyclopropylmethoxy-4-(2-methoxymethyl-pyrrolidin-1-yl)-2-methyl-quinoline;
93. (S)-4-(2-hydroxymethyl-pyrrolidin-1-yl)-2-methyl-quinolin-7-ol;
94. (S)-{1-[7-(2-fluoro-pyridin-3-ylmethoxy)-2-methyl-quinolin-4-yl]-pyrrolidin-2-yl}-methanol;
95. (S)-{1-[7-(2-chloro-pyridin-3-ylmethoxy)-2-methyl-quinolin-4-yl]-pyrrolidin-2-yl}-methanol;
96. (S)-2-[4-(2-hydroxymethyl-pyrrolidin-1-yl)-2-methyl-quinolin-7-yloxymethyl]-benzonitrile;
97. (S)-{1-[2-methyl-7-(pyridin-3-ylmethoxy)-quinolin-4-yl]-pyrrolidin-2-yl}-methanol;
98. (S)-5-[4-(2-hydroxymethyl-pyrrolidin-1-yl)-2-methyl-quinolin-7-yloxymethyl]-pyridine-2-carbonitrile;
99. 7-benzyloxy-6-fluoro-2-methyl-4-pyrrolidin-1-yl-quinoline;
100. 6-fluoro-2-methyl-4-pyrrolidin-1-yl-quinolin-7-ol;
101. 4-(6-fluoro-2-methyl-4-pyrrolidin-1-yl-quinolin-7-yloxymethyl)-benzonitrile;
102. 6-fuoro-2-methyl-7-(pyridin-3-ylmethoxy)-4-pyrrolidin-1-yl-quinoline;
103. 6-fluoro-7-(2-fluoro-pyridin-3-ylmethoxy)-2-methyl-4-pyrrolidin-1-yl-quinoline;
104. 7-(2-chloro-pyridin-3-ylmethoxy)-6-fluoro-2-methyl-4-pyrrolidin-1-yl-quinoline;
105. 6-fluoro-2-methyl-7-(2-methyl-pyridin-3-ylmethoxy)-4-pyrrolidin-1-yl-quinoline;
106. 3-(6-fluoro-2-methyl-4-pyrrolidin-1-yl-quinolin-7-yloxymethyl)-benzonitrile;
107. 2-(6-fluoro-2-methyl-4-pyrrolidin-1-yl-quinolin-7-yloxymethyl)-benzonitrile;
108. 7-cyclopropylmethoxy-6-fluoro-2-methyl-4-pyrrolidin-1-yl-quinoline;
109. 5-(6-fluoro-2-methyl-4-pyrrolidin-1-yl-quinolin-7-yloxymethyl)-pyridine-2-carbonitrile;
110. (R)-7-benzyloxy-4-(3-methoxy-pyrrolidin-1-yl)-2-methyl-quinoline;
111. (S)-7-benzyloxy-4-[3-(2-methoxy-ethoxy)-pyrrolidin-1-yl]-2-methyl-quinoline;
112. (S)-7-benzyloxy-4-(3-methoxy-pyrrolidin-1-yl)-2-methyl-quinoline;
113. (S)-7-benzyloxy-4-(3-cyclopropylmethoxy-pyrrolidin-1-yl)-2-methyl-quinoline;
114. (S)-7-benzyloxy-4-[3-(3-methoxy-propoxy)-pyrrolidin-1-yl]-2-methyl-quinoline;
115. 7-benzyloxy-2-methyl-4-{(3S)-3-[2-(tetrahydro-pyran-2-yloxy)-ethoxy]-pyrrolidin-1-yl}-quinoline;
116. (S)-4-[3-(2-methoxy-ethoxy)-pyrrolidin-1-yl]-2-methyl-quinolin-7-ol;
117. (S)-4-(3-methoxy-pyrrolidin-1-yl)-2-methyl-quinolin-7-ol;
118. (S)-4-(3-cyclopropylmethoxy-pyrrolidin-1-yl)-2-methyl-quinolin-7-ol;
119. (S)-4-[3-(3-methoxy-propoxy)-pyrrolidin-1-yl]-2-methyl-quinolin-7-ol;
120. 2-methyl-4-{(3S)-3-[2-(tetrahydro-pyran-2-yloxy)-ethoxy]-pyrrolidin-1-yl}-quinolin-7-ol;
121. (S)-4-{4-[3-(2-methoxy-ethoxy)-pyrrolidin-1-yl]-2-methyl-quinolin-7-yloxymethyl}-benzonitrile;

122. (S)-4-[4-(3-methoxy-pyrrolidin-1-yl)-2-methyl-quinolin-7-yloxymethyl]-benzonitrile;
123. (S)-4-[4-(3-cyclopropylmethoxy-pyrrolidin-1-yl)-2-methyl-quinolin-7-yloxymethyl]-benzonitrile;
124. (S)-4-{4-[3-(3-methoxy-propoxy)-pyrrolidin-1-yl]-2-methyl-quinolin-7-yloxymethyl}-benzonitrile;
125. (S)-4-{4-[3-(2-Hydroxy-ethoxy)-pyrrolidin-1-yl]-2-methyl-quinolin-7-yloxymethyl}-benzonitrile;
126. (S)-[1-(7-benzyloxy-6-fluoro-2-methyl-quinolin-4-yl)-pyrrolidin-2-yl]-methanol;
127. (S)-6-fluoro-4-(2-hydroxymethyl-pyrrolidin-1-yl)-2-methyl-quinolin-7-ol;
128. (S)-4-[6-fluoro-4-(2-hydroxymethyl-pyrrolidin-1-yl)-2-methyl-quinolin-7-yloxymethyl]-benzonitrile;
129. (S)-5-[6-fluoro-4-(2-hydroxymethyl-pyrrolidin-1-yl)-2-methyl-quinolin-7-yloxymethyl]-pyridine-2-carbonitrile;
130. (S)-4-[4-(3-hydroxy-pyrrolidin-1-yl)-2-methyl-quinolin-7-yloxymethyl]-benzonitrile;
131. (R)-4-[4-(3-hydroxy-pyrrolidin-1-yl)-2-methyl-quinolin-7-yloxymethyl]-benzonitrile;
132. (R,S)-4-[2-methyl-4-(2-methyl-pyrrolidin-1-yl)-quinolin-7-yloxymethyl]-benzonitrile;
133. (S)-4-[4-(2-hydroxymethyl-pyrrolidin-1-yl)-2-methyl-quinolin-7-yloxymethyl]-benzonitrile;
134. (R)-4-[4-(2-hydroxymethyl-pyrrolidin-1-yl)-2-methyl-quinolin-7-yloxymethyl]-benzonitrile;
135. (R)-4-[4-(3-dimethylamino-pyrrolidin-1-yl)-2-methyl-quinolin-7-yloxymethyl]-benzonitrile;
136. (S)-4-[4-(3-dimethylamino-pyrrolidin-1-yl)-2-methyl-quinolin-7-yloxymethyl]-benzonitrile;
137. (R)-4-[4-(2-methoxymethyl-pyrrolidin-1-yl)-2-methyl-quinolin-7-yloxymethyl]-benzonitrile;
138. (S)-4-[4-(2-methoxymethyl-pyrrolidin-1-yl)-2-methyl-quinolin-7-yloxymethyl]-benzonitrile;
139. (R,S)-4-[4-(2-isopropyl-pyrrolidin-1-yl)-2-methyl-quinolin-7-yloxymethyl]-benzonitrile;
140. (S)-1-[7-(4-cyano-benzyloxy)-2-methyl-quinolin-4-yl]-pyrrolidine-2-carboxylic acid methyl ester;
141. (R)-4-[2-methyl-4-(3-methylamino-pyrrolidin-1-yl)-quinolin-7-yloxymethyl]-benzonitrile;
142. (S)-4-[2-methyl-4-(3-methylamino-pyrrolidin-1-yl)-quinolin-7-yloxymethyl]-benzonitrile;
143. 4-(2-methyl-4-piperidin-1-yl-quinolin-7-yloxymethyl)-benzonitrile;
144. 4-(2-methyl-4-morpholin-4-yl-quinolin-7-yloxymethyl)-benzonitrile;
145. (R,S)-4-[4-(3-diethylamino-pyrrolidin-1-yl)-2-methyl-quinolin-7-yloxymethyl]-benzonitrile;
146. (R,S)-4-[2-methyl-4-(3-pyridin-2-yl-pyrrolidin-1-yl)-quinolin-7-yloxymethyl]-benzonitrile;
147. (R,S)-4-[2-methyl-4-(3-pyridin-4-yl-pyrrolidin-1-yl)-quinolin-7-yloxymethyl]-benzonitrile;
148. (S)-4-[2-methyl-4-(2-pyrrolidin-1-ylmethyl-pyrrolidin-1-yl)-quinolin-7-yloxymethyl]-benzonitrile;
149. (R,S)-4-[4-(3-methanesulfonyl-pyrrolidin-1-yl)-2-methyl-quinolin-7-yloxymethyl]-benzonitrile;
150. (R,S)-4-[2-methyl-4-(3-methyl-piperidin-1-yl)-quinolin-7-yloxymethyl]-benzonitrile;
151. 4-[4-(1,4-dioxa-8-aza-spiro[4.5] dec-8-yl)-2-methyl-quinolin-7-yloxymethyl]-benzonitrile and
152. (R,S)-4-[4-(3-hydroxymethyl-piperidin-1-yl)-2-methyl-quinolin-7-yloxymethyl]-benzonitrile.

Examples of particularly preferred compounds of formula (I) are 2-methyl-4-pyrrolidin-1-yl-quinolin-7-ol;
7-(3-methoxy-benzyloxy)-2-methyl-4-pyrrolidin-1-yl-quinoline;
2-(2-methyl-4-pyrrolidin-1-yl-quinolin-7-yloxymethyl)-benzonitrile;
4-(2-methyl-4-pyrrolidin-1-yl-quinolin-7-yloxymethyl)-benzonitrile;
7-(3-chloro-benzyloxy)-2-methyl-4-pyrrolidin-1-yl-quinoline;
7-(4-chloro-benzyloxy)-2-methyl-4-pyrrolidin-1-yl-quinoline;
(S)-4-[4-(3-ethoxy-pyrrolidin-1-yl)-2-methyl-quinolin-7-yloxymethyl]-benzonitrile;
6-butyl-4-pyrrolidin-1-yl-quinolin-7-ol;
4-(6-butyl-4-pyrrolidin-1-yl-quinolin-7-yloxymethyl)-benzonitrile;
4-azepan-1-yl-2-methyl-7-(pyridin-4-ylmethoxy)-quinoline;
4-(4-azepan-1-yl-2-methyl-quinolin-7-yloxymethyl)-benzonitrile;
3-(4-azepan-1-yl-2-methyl-quinolin-7-yloxymethyl)-benzonitrile;
7-(2-chloro-pyridin-3-ylmethoxy)-2-methyl-4-pyrrolidin-1-yl-quinoline;
(S) 4-(3-ethoxy-pyrrolidin-1-yl)-7-(2-fluoro-pyridin-3-ylmethoxy)-2-methyl-quinoline;
(S) 7-(2-chloro-pyridin-3-ylmethoxy)-4-(3-ethoxy-pyrrolidin-1-yl)-2-methyl-quinoline;
(S)-7-(2-chloro-pyridin-3-ylmethoxy)-4-(2-methoxymethyl-pyrrolidin-1-yl)-2-methyl-quinoline;
(S)-7-(2-fluoro-pyridin-3-ylmethoxy)-4-(2-methoxymethyl-pyrrolidin-1-yl)-2-methyl-quinoline;
(S)-{1-[7-(2-fluoro-pyridin-3-ylmethoxy)-2-methyl-quinolin-4-yl]-pyrrolidin-2-yl}-methanol;
(S)-{1-[7-(2-chloro-pyridin-3-ylmethoxy)-2-methyl-quinolin-4-yl]-pyrrolidin-2-yl}-methanol;
4-(6-fluoro-2-methyl-4-pyrrolidin-1-yl-quinolin-7-yloxymethyl)-benzonitrile;
6-fluoro-7-(2-fluoro-pyridin-3-ylmethoxy)-2-methyl-4-pyrrolidin-1-yl-quinoline;
7-(2-chloro-pyridin-3-ylmethoxy)-6-fluoro-2-methyl-4-pyrrolidin-1-yl-quinoline;
(S)-4-[4-(3-methoxy-pyrrolidin-1-yl)-2-methyl-quinolin-7-yloxymethyl]-benzonitrile;
(S)-4-[6-fluoro-4-(2-hydroxymethyl-pyrrolidin-1-yl)-2-methyl-quinolin-7-yloxymethyl]-benzonitrile;
(S)-4-[4-(3-hydroxy-pyrrolidin-1-yl)-2-methyl-quinolin-7-yloxymethyl]-benzonitrile;
(R)-4-[4-(3-hydroxy-pyrrolidin-1-yl)-2-methyl-quinolin-7-yloxymethyl]-benzonitrile;
(S)-4-[4-(2-hydroxymethyl-pyrrolidin-1-yl)-2-methyl-quinolin-7-yloxymethyl]-benzonitrile and
(R)-4-[4-(2-hydroxymethyl-pyrrolidin-1-yl)-2-methyl-quinolin-7-yloxymethyl]-benzonitrile.

Processes for the manufacture of compounds of formula I are an object of the invention.

The substituents and indices used in the following description of the processes have the significance given above unless indicated to the contrary.

Compounds of formula I can be obtained according to scheme 1 from compounds of formula Ia comprising $R^2$ substituents according to the above definition by an alkylation reaction with, e.g. K₂CO₃ as a base and in a suited solvent such as DMF. The alkylation reaction to introduce R¹ can also be performed on the intermediates described below, prior to implementation of the substituents in 4-quinoline poition by inverting the reaction steps.

Scheme 1

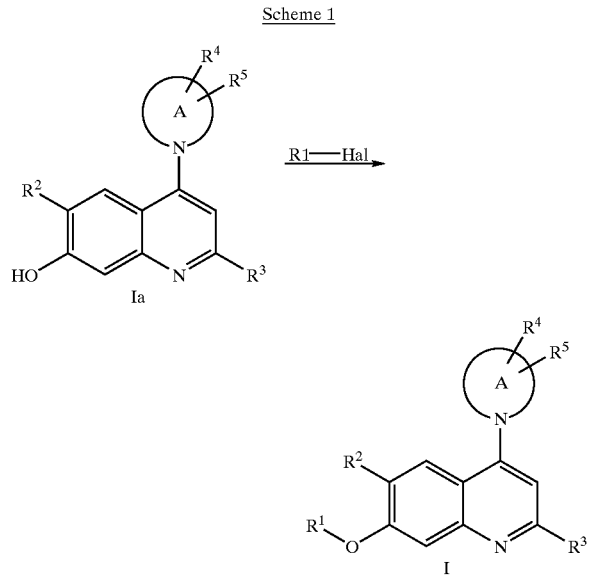

Alternatively, compounds of formula I can be obtained from Ib, according to scheme 2, by an alkylation reaction as above to give compounds of formula 1c and subsequent Pd catalysed C/O, C/N or C/C bond forming reactions in analogy to known procedures. Thus, substituted alkoxy, and amino groups can be introduced via a C/O, C/N bond forming reaction under Buchwald conditions, from the corresponding alkohols and amines with, for example, Pd(OAc)₂ as catalyst, BINAP (2,2 bis(dipenylphosphino)-1,1-binaphthyl) as chelating phosphine ligand and with NaOtBu as a base—in a solvent such as toluene and at elevated temperature (S. L. Buchwald in: J Am. Chem. Soc. 1996, p. 10333 and Acc. Chem Res. 1998, p 805 for the general method).

With repect to Pd catalysed C/C bond forming methods to introduce the above defined substituted alkyl and (hetero) aryl groups: This can be achieved via Suzuki-type coupling (for aryl, heteroaryl substitutents) starting from well described or commercial aryl or heteroaryl boronic acids with, for example, Pd(PPh₃)₄ as catalyst, Na₂CO₃ as base, in DMF at elevated temperature (general method: Synth. Commun. 1991, p 513). An alternative consists in using the correponding aryl or heteroaryl stannanes in a Stille-type coupling (for general method: Ang. Chem IE, 1986, 508).

Procedures to introduce arylalky, heteroarylalkyl consists of applying the reaction discussed above or to use Pd catalysed C/C bond formation under Negishi conditions, starting from the known arylalkyl, heteroarylalkyl Li or Mg salts, with Pd(PPh₃)₄ as catalyst, in the presence of ZnCl₂ and in THF as solvent (general method: Acc. Chem. Res. 1982, p340). Other methods (e.g for arylethyl, heteroarylethyl group introduction) consists of performing a Heck-type coupling, starting from a correponding (hetero)aryl olefine and 1c, with Pd₂(dba)₃ as catalyst, P(t-Bu)₃ as phosphine ligand, CsCO₃ as base in DMF as solvent at elevated temperature. (G. C. Fu in: J. Org. Chem. 1999, p. 10 for recent application of the reaction). The (hetero) arylalkene condensation products can then be reduced further by hydrogenation.

A method to introduce alkinyl groups consists of reacting an alkine with 1c under the Sonogashira conditions (review: Org. Prep. Proceed. Int. 1995, p127) with Pd(PPh₃)₄ as catalyst, in the presence of CuI and with triethyl amine as a base. Alkenyl dervivatives are obtained from alkenes via Heck coupling as pointed out above, and alkyl as R² substituent can be obtained from the corresponding alkenes by hydrogenation.

An alternative sequence to perform above discussed Stille-, Negishi and Suzuki-type condensations consisits of performing an halogen/metal exchange reaction from Ic, to obtain the correponding stannanes, Li or Mg salts or boronic acids. This is then followed by a Pd-catalysed condensation with appropriate halogenides (R²Hal) according to the general methods given above.

Scheme 2

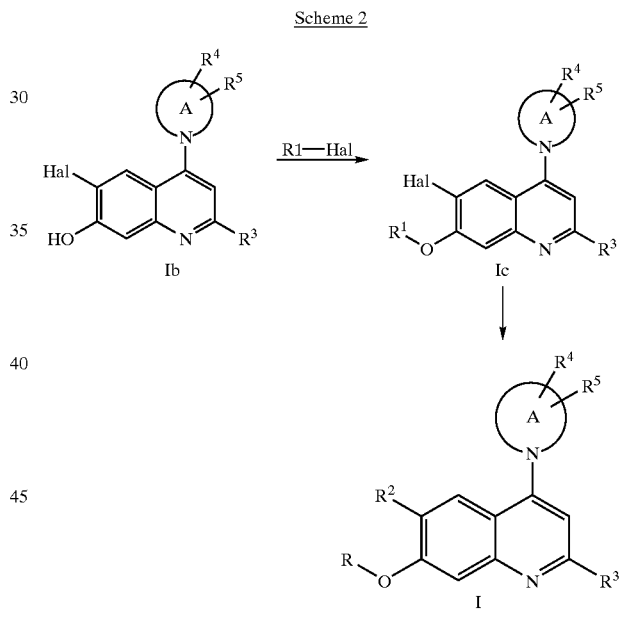

R² is halogen, alkyl, alkenyl, alkinyl, aralkyl, heteroarylalkyl, hydroxyalkyl, alkoxy, alkoxyalkoxy, hydroxyalkoxyalkyl, aryloxy, arylamino, heteroarylamino, NH₂—, mono- or dialkylamino, heterocyclyl, arylalkylamino, heteroarylalkylamino, aryl, heteroaryl, arylalkoxy or heteroarylalkoxy.

Compounds of formula I can also be prepared according to scheme 3 from compounds of formula II with appropriate alkohols (R¹OH) in a Pd catalysed C/O bond forming reaction under Buchwald conditions as discussed above or by Ullman-type rection with, for example CuCl, in a solvent such as DMF, in analogy to a method described by J. A. Ragan: Synthesis 1998, p1599.

Scheme 3

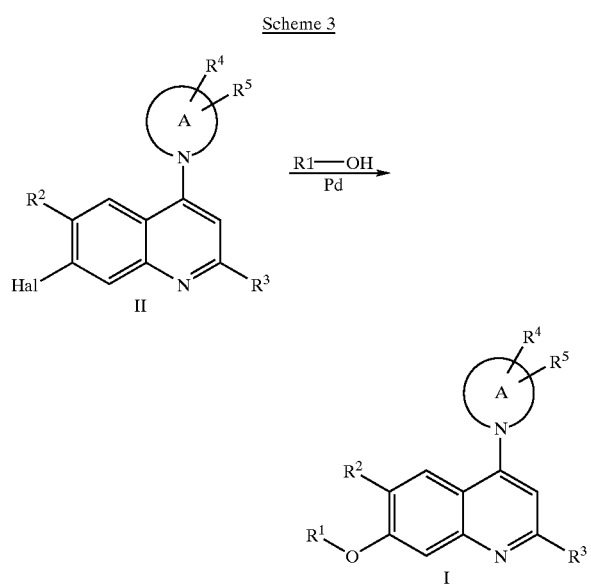

Compounds of formula Ia, b and II can be prepared as follows:

The preparation of compounds according to formula Ia$_1$, wherein R$^3$ is not NH$_2$—, alkylamino, dialkylamino or alkoxy, is achieved is according to scheme 4, starting from appropriate anilines which are either known in the literature or which can being prepared by standard procedures known in the art. Thus, condensation with corresponding alkoxy-carbonyl ketones or aldehydes in the presence of p-toluenesulfonic acid, in refluxing cyclohexane and under capture of water produced during the reaction, the enamine derivatives of formula IV are obtained. Subsequent ring closure is achieved on heating at 250° C. in a high boiling solvent such as Dowtherm A to give compounds of formula V. Transformation to the corresponding chloro quinoline derivatives of formula VI is performed on treatment with POCl$_3$ under reflux, a standard method known in the literature. Subsequent reaction with corresponding amines as defined above, either using a large excess of amine without solvent or on reaction with a 2-fold access, in a suited solvent such as ethanol or THF and in the presence of catalytic amounts of NaI and with pyridine as a base, gives compounds of formula VII$_1$. The amines used are either substituted with R$^4$, R$^5$ groups as defined or the groups can be introduced by functional group conversion as known in the art. P is a protecting group such as benzyl, ally or tert.butyl. Deprotection under standard conditions known in the art gives rise to Ia$_1$. Compounds of formula Ia$_1$ can also be obtained from the corresponding methoxy derivatives (P=Me, formula VII$_1$) on methyl ether cleavage with BBr$_3$ in CH$_2$Cl$_2$ as a solvent.

Scheme 4

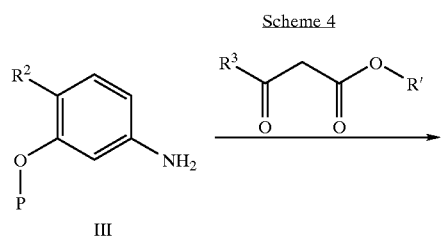

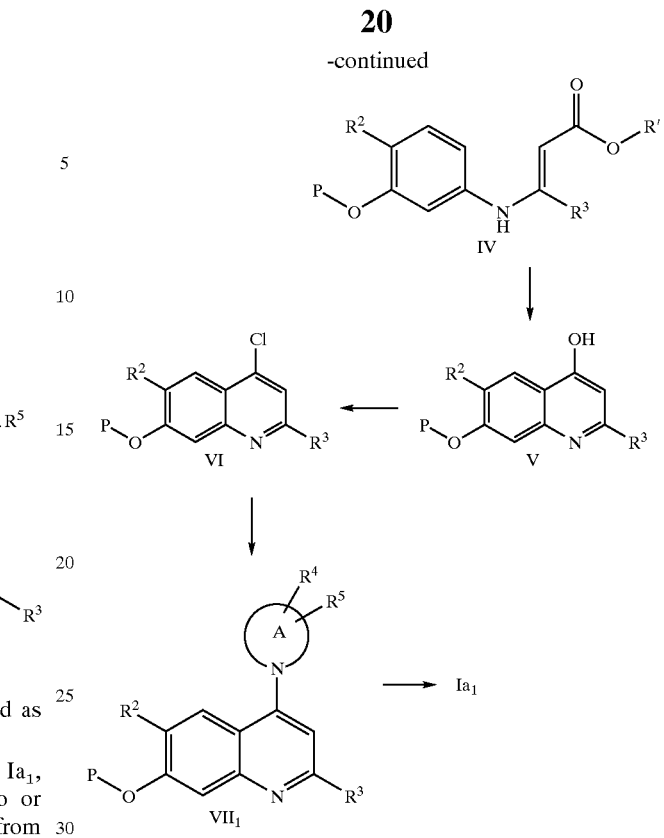

R$^3$ is hydrogen or alkyl;
P is a protecting group such as e.g. benzyl, allyl or tert.butyl;
R' is methyl or ethyl.

Compounds of formula Ib$_1$ and II$_1$ (R$^3$ not NH$_2$—, alkylamino, dialkylamino or alkoxy) are prepared as described above from appropriately substituted anilines according to scheme 4.

Compounds of formula Ia$_2$, with R$^3$ equaling NH$_2$—, alkylamino, dialkylamino can be prepared from anilines of formula III, by condensation with alkyl cyanoacetates, ring closure and subsequent functional group transformations as described above. The corresponding compounds with alkylamino or dialkylamino as R$^3$ substitutents can be obtained from, for example, intermediate IX or VII$_2$ (R$^3$=NH$_2$) by selective N-alkylation.

In analogy to the sequence described in scheme 5 and starting from the appropriate anilines there can be obtained the compounds of fomula Ib$_2$ and II$_2$ (R$^3$ equaling NH$_2$— or alkylamino or dialkylamino).

Scheme 5

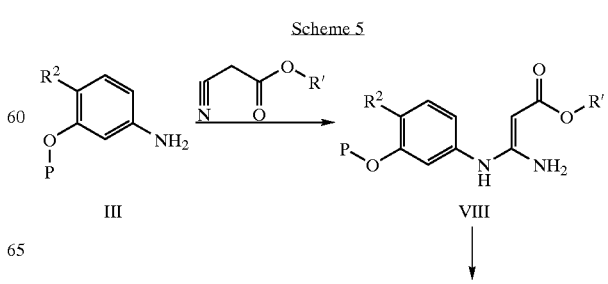

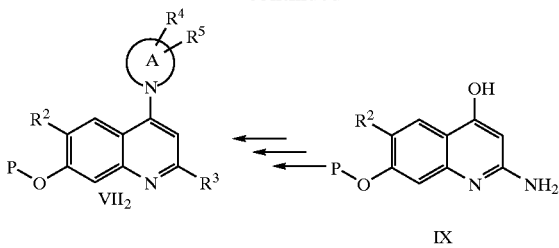

$R^3$ is $NH_2$—, alkylamino or dialkylamino;
R' is methyl or ethyl;
P is a protecting group such benzyl, allyl or tert.-butyl.

A further method to prepare compounds of formula $Ia_2$, $Ib_2$ and $II_2$ comprises condensation of anilines of formula III with malonic esters to give compounds of formula X. Subsequent ring closure provides the 2,4-dihydroxyquinolines of formula XI. Subsequent chlorination with $POCl_3$ gives then the 2,4-dichloro-quinolines of formula XII which can be selectively transformed to compounds of type $VII_2$ by sequential substitution reactions with the corresponding amines—in analogy to known reactions in the literature. By this procedure there can also be obtained compound of formula $VII_2$ ($R^3$ is alkoxy) via sequential treatment of XII with correponding amines and alkohols. The compounds $Ib_2$, $II_2$ can be prepared in analogy according to scheme 6.

Preferred procedures are according to schemes 1, 2 and 5.

Scheme 6

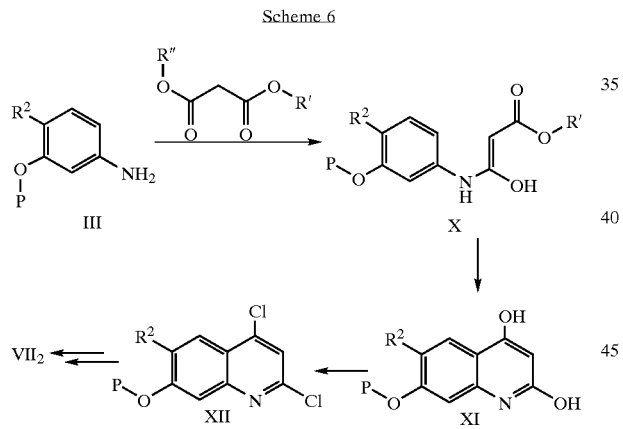

$R^3$ is $NH_2$—, alkylamino, dialkyl amino or alkoxy;
R' is methyl or ethyl;
R" is methyl or ethyl.

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases.

The conversion of compounds of formula I into pharmaceutically usable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP) or N,N-dicylohexylcarbodiimide (DCCI) to produce the carboxylic ester or carboxylic amide.

A preferred process for the preparation of a compound of formula I comprises one of the following reactions:

a) reaction of a compound of the formula Ia in the presence of a compound of the formula $R^1$-Hal

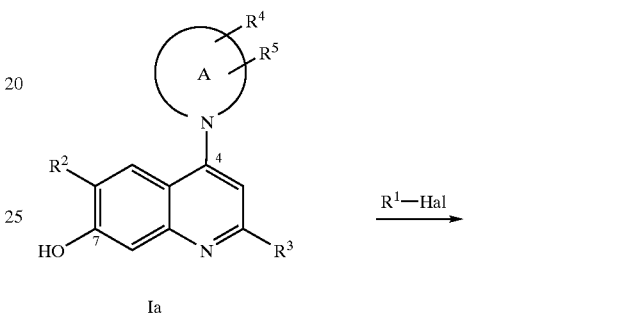

wherein $R^1$, $R^2$, $R^3$, $R^4$, $R^5$ and A are as defined before and Hal is halogen; or b) Pd catalyzed C/O, C/N or C/C bond forming reaction of a compound of formula Ic in order to obtain a compound of formula I

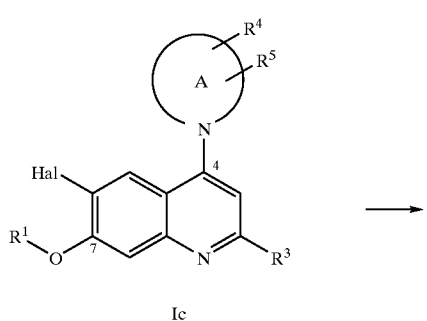

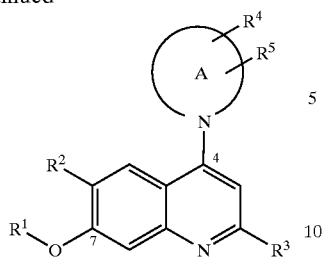

I wherein $R^1$, $R^2$, $R^3$, $R^4$, $R^5$ and A are defined as before and Hal is halogen, preferably chloro, bromo or iodo. Preferred is the reaction of a compound according to formula Ic under Buchwald conditions (S. L. Buchwald in: J Am. Chem. Soc. 1996, p. 10333 and Acc. Chem Res. 1998, p 805 for the general method), particularly in the presence of $Pd(OAc)_2$, BINAP and a base such as NaOtBu with a corresponding alcohol or amine in order to form a compound of formula I, wherein $R^2$ means alkoxy or amino. Further preferred is the reaction of a compound of formula Ic under Suzuki-type coupling conditions (general method: Synth. Commun. 1991, p 513) in the presence of corresponding arylboronic acids or heteroarylboronic acids in order to form a compound of formula I, wherein $R^2$ means aryl or heteroaryl. Also preferred is the reaction of a compound of formula Ic under Stille coupling conditions (for general method: Ang. Chem IE, 1986, 508) in the presence of corresponding arylstannanes or heteroarylstannanes in order to form a compound of formula I, wherein $R^2$ means aryl or heteroaryl. Further preferred is the reaction of a compound of formula Ic under Sonogashira conditions (review: Org. Prep. Proceed. Int. 1995, p127), particularly in the presence of CuI and a base such as triethylamine in the presence of corresponding alkines in order to form a compound of formula I, wherein $R^2$ means alkinyl; or c) a halogen/metal exchange reaction of a compound of formula Ic as defined in step b) and subsequent Pd catalyzed condensation with a halogenide of the formula $R^2$-Hal to yield a compound of formula I, wherein $R^1$, $R^3$, $R^4$, $R^5$ and A are as defined as before, Hal is halogen and $R^2$ is alkenyl, alkinyl, alkoxy, alkoxyalkoxy, aryloxy, arylamino, heteroarylamino, $NH_2$—, monoalkylamino, dialkylamino, arylalkylamino, heteroarylalkylamino, aryl, arylalkoxy or heteroarylalkoxy; or d) reaction of a compound of formula II in the presence of an alcohol of the formula $R^1$—OH and a palladium catalyst in order to obtain a compound of formula I

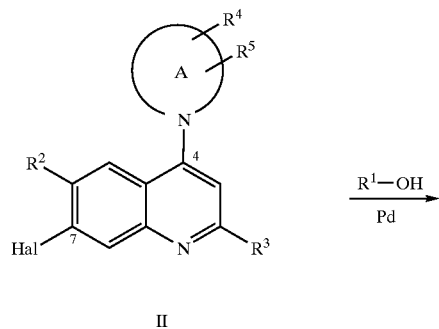

II

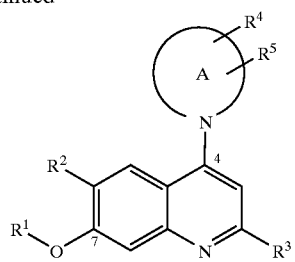

I wherein $R^2$, $R^3$, $R^4$, $R^5$ and A are defined as before, Hal is halogen and $R^1$ is hydrogen, alkyl, alkoxyalkyl, alkenyl, alkinyl, hydroxyalkyl, aralkyl, heterocyclylalkyl, cycloalkylalkyl, $NH_2$—$SO_2$—, monoalkylamino-$SO_2$—, dialkylamino-$SO_2$—, alkyl-$SO_2$—, aryl, $NH_2$-alkyl, monoalkylaminoalkyl, dialkylaminoalkyl, alkoxycarbonylalkyl, carboxyalkyl, aryl-$SO_2$—O-alkyl, cycloalkyl or cycloalkylalkyl.

A particularly preferred process for the preparation of a compound of formula I comprises one of the reactions a), c) or d) as mentioned before.

Preferred intermediates are:

7-benzyloxy-4-chloro-2-methyl-quinoline;
7-benzyloxy-6-butyl-4-chloro-quinoline hydrochloride;
6-bromo-4-chloro-7-methoxy-2-methyl-quinoline.

The compounds of formula I described above for use as therapeutically active substances are a further object of the invention.

Also an object of the invention are compounds described above for the production of medicaments for the prophylaxis and therapy of illnesses which are caused by disorders associated with the NPY receptor, particularly for the production of medicaments for the prophylaxis and therapy of arthritis, cardiovascular diseases, diabetes, renal failure and particularly eating disorders and obesity.

Likewise an object of the invention are pharmaceutical compositions containing a compound of formula I described above and a therapeutically inert carrier.

An object of the invention is also the use of the compounds described above for the production of medicaments, particularly for the treatment and prophylaxis of arthritis, cardiovascular diseases, diabetes, renal failure and particularly eating disorders and obesity.

A further object of the invention comprises compounds which are manufactured according to one of the described processes.

A further object of the invention is a method for the treatment and prophylaxis of arthritis, cardiovascular diseases, diabetes, renal failure and particularly eating disorders and obesity whereby an effective amount of a compound described above is administered.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Assay Procedures

Cloning of Mouse NPY5 Receptor cDNAs

The full-length cDNA encoding the mouse NPY5 (mNPY5) receptor was amplified from mouse brain cDNA using specific primers, designed based on the published sequence, and Pfu DNA-Polymerase (Stratagene). The amplification product was subcloned into the mammalian expression vector pcDNA3 using Eco RI and XhoI restriction sites. Positive clones were sequenced and one clone, encoding the published sequence was selected for generation of stable cell clones.

Stable Transfection

Human embryonic kidney 293 (HEK293) cells were transfected with 10 μg mNPY5 DNA using the lipofectamine reagent (Gibco BRL) according to the manufacturer's instruction. Two days after transfection, geneticin selection (1 mg/ml) was initiated and several stable clones were isolated. One clone was further used for pharmacological characterization.

Radioligand Competition Binding

Human embryonic kidney 293 cells (HEK293), expressing recombinant mouse NPY5-receptor (mNPY5) were broken by three freeze/thawing cycles in hypotonic Tris buffer (5 mM, pH 7.4, 1 mM $MgCl_2$), homogenized and centrifuged at 72,000×g for 15 min. The pellet was washed twice with 75 mM Tris buffer, pH 7.4, containing 25 mM $MgCl_2$ and 250 mM sucrose, 0.1 mM phenylmethylsulfonylfluoride and 0.1 mM 1,10-pheneanthrolin, resuspended in the same buffer and stored in aliquots at −80° C. Protein was determined according to the method of Lowry using bovine serum albumine (BSA) as a standard.

Radioligand competition binding assays were performed in 250 μl 25 mM Hepes buffer (pH 7.4, 2.5 mM $CaCl_2$, 1 mM $MgCl_2$, 1% bovine serum albumine, and 0.01% $NaN_3$ containing 5 μg protein, 100 pM [$^{125}$I]labelled peptide YY (PYY) and 10 μL DMSO containing increasing amounts of unlabelled test compounds. After incubation for 1 h at 22° C., bound and free ligand are separated by filtration over glass fibre filters. Non specific binding is assessed in the presence of 1 μM unlabelled PYY. Specific binding is defined as the difference between total binding and non specific binding. $IC_{50}$ values are defined as the concentration of antagonist that displaces 50% of the binding of [$^{125}$I] labelled neuropeptide Y. It is determined by linear regression analysis after logit/log transformation of the binding data.

Results obtained in the foregoing test using representative compounds of the invention as the test compounds are shown in the following table:

| Compound | NPY5-R (mouse) $IC_{50}$ (nM) |
| --- | --- |
| 7-cyclopropylmethoxy-2-methyl-4-pyrrolidin-1-yl-quinoline (example 5) | 27 |

| Compound | NPY5-R (mouse) $IC_{50}$ (nM) |
| --- | --- |
| 6-butyl-4-pyrrolidin-1-yl-quinolin-7-ol (example 34) | 9.9 |

Preferred compounds as described above have $IC_{50}$ values below 1000 nM; more preferred compounds have $IC_{50}$ values below 100 nM, particularly below 10 nM. Most preferred compounds have $IC_{50}$ values below 2 nM. These results have been obtained by using the foregoing test.

The compounds of formula I and their pharmaceutically usable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically usable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically usable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1 a) A mixture of 534 mg (1.8 mmol) of 7-benzyloxy-4-chloro-2-methyl-quinoline and 3.77 ml (45 mmol) pyrrolidine was heated at 80° C. (oil bath temperature) under an argon atmosphere for 23 h after which time the reaction was completed according to HPLC analysis. The reaction was partitioned between EtOAc and water, the aqueous layer was extracted once with EtOAc, the combined organic layers were washed with water then saturated NaCl solution, dried over magnesium sulphate and concentrated in vacuo. The residue was applied to silica gel column with $CH_2Cl_2$/MeOH/$NH_4OH$ (19:1:0.05) as eluent. Combination of the purified fractions and concentration in vacuo gave 430 mg (74.5%) of the 7-benzyloxy-2-methyl-4-pyrrolidin-1-yl-quinoline as a brown solid. ISP mass spectrum, m/e: 319.4 (M+1 calculated for $C_{21}H_{22}N_2O$: 319).

Preparation of the Starting Material:

b) 20 g (98.4 mmol) of 3-benyloxyaniline, 12.6 ml (0.984 mmol) of ethyl acetoacetate and 0.189 g (1 mmol) of p-toluenesulfonic acid monohydrate in 32 ml of cyclohexane were heated at reflux for 5.5 h in the presence of a water separator funnel. The reaction mixture was cooled to RT, some solid material was filtered off by suction and the filtrate was concentrated in vacuo to give 30.6 g (99%) of the desired 3-(3-benzyloxy-phenylamino)-but-2-enoic acid ethyl ester as a yellow oil. This was used without further purification in the next reaction step.

c) 3.67 g (11.8 mmol) of 3-(3-benzyloxy-phenylamino)-but-2-enoic acid ethyl ester were added dropwise within 20 minutes to 5.5 ml of Dowtherm A heated at 250° C. (metal bath temperature). The solution was stirred further 10 minutes at 250° C. (bath temperature), cooled to RT and then treated with 20 ml of heptane. The brown viscous oil that had formed was isolated and triturated with 45 ml of AcOEt. The brown solid obtained was filtered off by suction, washed with AcOEt and dried in a high vacuum to give 1.19 g (35%) of 7-benzyloxy-2-methyl-quinolin-4-ol. ISP mass spectrum, m/e: 266.3 (M+1 calculated for $C_{17}H_{15}NO_2$: 266).

d) 1.15 g (3.99 mmol) of 7-benzyloxy-2-methyl-quinolin-4-ol in 7.46 ml (79.8 mmol) of $POCl_3$ were heated at 130° C. (oil bath temperature) for 1 h 40 min until completion of the reaction according to TLC analysis. The reaction mixture was cooled to RT and the solvent was removed in vacuo. The residue was taken up in ice water and stirred for 2 h. The pH was adjusted to values between pH 9–10 with concentrated $NH_4Cl$, the brown solid which precipitated was filtered off by suction, washed with water and subsequently dried in a high vacuum. This gave 1 g (84.5%) of 7-benzyloxy-4-chloro-2-methyl-quinoline as a brown solid. EI mass spectrum, m/e: 283.1 (M+1 calculated for $C_{17}H_{14}ClNO$: 283).

Example 2

A solution of 13 g of 7-benzyloxy-2-methyl-4-pyrrolidin-1-yl-quinoline, product of example 1, dissolved in 750 ml of MeOH was treated with 4 g of palladium on charcoal (10%) and then hydrogenated at RT for 1.5 h until HPLC analysis indicated the completion of the reaction. The catalyst was filtered off, washed with water) and the solution was concentrated in vacuo. The solid that precipitated was collected by filtration and dried in a high vacuum to give 8.9 g (96.2%) of 2-methyl-4-pyrrolidin-1-yl-quinolin-7-ol as an amorphous yellow solid. ISP mass spectrum, m/e: 229.2 (M+1 calculated for $C_{14}H_{16}N_2O$: 229).

Example 3

229.4 mg (1 mmol) of 2-methyl-4-pyrrolidin-1-yl-quinolin-7-ol, product of example 2, were suspended under an argon atmosphere in 20 ml of DMF, 0.6 g (1.2 mmol) of molecular sieves (4 nm) were added followed by 138 mg (1.2 mmol) of potassium tert-butoxide, and the mixture was stirred for 1 h at RT. It was then cooled to 0° C., treated with 0.13 ml (1.2 mmol) N,N-dimethylsulfamoyl chloride and stirred for 3 h at 0° C. The reaction mixture was partitioned between EtOAc and water, the aqueous layer was extracted twice with EtOAc, the combined organic layers were washed with water then with saturated NaCl solution, dried over magnesium sulphate and concentrated in vacuo. The residue was triturated with diethyl ether; the viscous oil obtained was filtered off by suction and dried in a high vacuum. Upon further triturating with heptane solid material was obtained which was dried in a high vacuum to give 100 mg (29.3%) of dimethyl-sulfamic acid 2-methyl-4-pyrrolidin-1-yl-quinolin-7-yl ester as an off-white solid. ISP mass spectrum, m/e: 336.2 (M+1 calculated for $C_{16}H_{21}N_3O_3S$: 336).

Example 4

In analogy to example 3, from 2-methyl-4-pyrrolidin-1-yl-quinolin-7-ol, product of example 2, and methanesulfonyl chloride there was obtained methanesulfonic acid 2-methyl-4-pyrrolidin-1-yl-quinolin-7-yl ester as an off-white solid. ISP mass spectrum, m/e: 307.3 (M+1 calculated for $C_{15}H_{18}N_3O_3S$: 307).

Example 5

In analogy to example 3, from 2-methyl-4-pyrrolidin-1-yl-quinolin-7-ol, product of example 2, and cyclopropylmethyl bromide—with reaction times of 19 h (0° C.) and isolation of the product as hydrochloride, via treatment of the reaction product with HCl-saturated diethyl ether—there was obtained 7-cyclopropylmethoxy-2-methyl-4-pyrrolidin-1-yl-quinoline hydrochloride as a white solid. ISP mass spectrum, m/e: 283.2 (M+1 calculated for $C_{18}H_{22}N_2O$: 283).

Example 6

A mixture of 114 mg (0.5 mmol) of 2-methyl-4-pyrrolidin-1-yl-quinolin-7-ol, product of example 2, 166 mg (0.6 mmol) of potassium carbonate and 84 µl (0.6 mmol) of 3-methoxybenzyl chloride was heated at 80° C. in 8 ml of DMF under an argon atmosphere for 23 h. The mixture was cooled to RT and partitioned between EtOAc and water. The organic layer was separated, washed with water then saturated NaCl solution, dried over magnesium sulphate and concentrated in vacuo. The residue was taken up in diethyl ether and some not dissolved material was removed by filtration. The filtrate was treated under stirring with 0.25 ml of 3N HCL in MeOH and stirring was continued for 1 h. The solid that precipitated was filtered off by suction and dried in a high vacuum to give 138 mg (69.7%) of 7-(3-methoxy-benzyloxy)-2-methyl-4-pyrrolidin-1-yl-quinoline hydrochloride as an light-yellow solid. ISP mass spectrum, m/e: 349.4 (M+1 calculated for $C_{22}H_{24}N_2O_2$: 349).

Example 7

In analogy to example 6 there was prepared: on reaction of 2-methyl-4-pyrrolidin-1-yl-quinolin-7-ol with methyl iodide, 7-methoxy-2-methyl-4-pyrrolidin-1-yl-quinoline hydrochloride as an off-white solid. ISP mass spectrum, m/e: 243.3 (M+1 calculated for $C_{15}H_{18}N_2O$: 243).

Example 8

In analogy to example 6 there was prepared: on reaction of 2-methyl-4-pyrrolidin-1-yl-quinolin-7-ol with 2-picolyl choride, whereby the product was isolated as free base, 2-methyl-7-(pyridin-2-ylmethoxy)-4-pyrrolidin-1-yl-quinoline as a light brown solid. ISP mass spectrum, m/e: 320.4 (M+1 calculated for $C_{20}H_{21}N_3O$: 320).

Example 9

In analogy to example 6 there was prepared: on reaction of 2-methyl-4-pyrrolidin-1-yl-quinolin-7-ol with allyl bromide, whereby the product was isolated as free base, 7-allyloxy-2-methyl-4-pyrrolidin-1-yl-quinoline as a light yellow solid. EI mass spectrum, m/e: 268.2 (M calculated for $C_{17}H_{20}N_2O$: 268).

Example 10

In analogy to example 6 there was prepared: on reaction of 2-methyl-4-pyrrolidin-1-yl-quinolin-7-ol with isobutyl bromide, 7-isobutoxy-2-methyl-4-pyrrolidin-1-yl-quinoline hydrochloride as a white solid. ISP mass spectrum, m/e: 285.3 (M+1 calculated for $C_{18}H_{24}N_2O$: 285).

Example 11

In analogy to example 6 there was prepared: on reaction of 2-methyl-4-pyrrolidin-1-yl-quinolin-7-ol with 2-methoxybenzyl chloride, 7-(2-methoxy-benzyloxy)-2-methyl-4-pyrrolidin-1-yl-quinoline hydrochloride as an off-white solid. ISP mass spectrum, m/e: 349.4 (M+1 calculated for $C_{22}H_{24}N_2O_2$: 349).

Example 12

In analogy to example 6 there was prepared: on reaction of 2-methyl-4-pyrrolidin-1-yl-quinolin-7-ol with tetrahydrofurfuryl bromide, whereby the product was isolated as free base, (rac) 2-methyl-4-pyrrolidin-1-yl-7-(tetrahydro-furan-2-ylmethoxy)-quinoline as a yellow-brown waxy solid. ISP mass spectrum, m/e: 313.2 (M+1 calculated for $C_{19}H_{24}N_2O_2$: 313).

Example 13

In analogy to example 6 there was prepared: on reaction of 2-methyl-4-pyrrolidin-1-yl-quinolin-7-ol with of 4-methoxybenzyl chloride, 7-(4-methoxy-benzyloxy)-2-methyl-4-pyrrolidin-1-yl-quinoline hydrochloride as a light-yellow solid. ISP mass spectrum, m/e: 349.4 (M+1 calculated for $C_{22}H_{24}N_2O_2$: 349).

Example 14

In analogy to example 6 there was prepared: on reaction of 2-methyl-4-pyrrolidin-1-yl-quinolin-7-ol with 2-bromomethyl benzonitrile, whereby the product was isolated as free base, 2-(2-methyl-4-pyrrolidin-1-yl-quinolin-7-yloxymethyl)-benzonitrile as a brown solid. ISP mass spectrum, m/e: 344.4 (M+1 calculated for $C_{22}H_{21}N_3O$: 344).

Example 15

In analogy to example 6 there was prepared: on reaction of 2-methyl-4-pyrrolidin-1-yl-quinolin-7-ol with 4-bromomethyl benzonitrile whereby the product was isolated as free base, 4-(2-methyl-4-pyrrolidin-1-yl-quinolin-7-yloxymethyl)-benzonitrile as a brown solid. ISP mass spectrum, m/e: 344.4 (M+1 calculated for $C_{22}H_{21}N_3O$: 344).

Example 16

In analogy to example 6 there was prepared: on reaction of 2-methyl-4-pyrrolidin-1-yl-quinolin-7-ol with 2-(trifluoromethyl)-benzyl chloride, 2-methyl-4-pyrrolidin-1-yl-7-(2-trifluoromethyl-benzyloxy)-quinoline hydrochloride as a white solid. ISP mass spectrum, m/e: 387.4 (M+1 calculated for $C_{22}H_{21}F_3N_2O_2$: 387).

Example 17

In analogy to example 6 there was prepared: on reaction of 2-methyl-4-pyrrolidin-1-yl-quinolin-7-ol with of 3-(trifluoromethyl)-benzyl chloride, 2-methyl-4-pyrrolidin-1-yl-7-(3-trifluoromethyl-benzyloxy)-quinoline hydrochloride as an off-white solid. ISP mass spectrum, m/e: 387.4 (M+1 calculated for $C_{22}H_{21}F_3N_2O_2$: 387).

Example 18

In analogy to example 6 there was prepared: on reaction of 2-methyl-4-pyrrolidin-1-yl-quinolin-7-ol with of 4-(trifluoromethyl)-benzyl chloride, 2-methyl-4-pyrrolidin-1-yl-7-(4-trifluoromethyl-benzyloxy)-quinoline hydrochloride as an off-white solid. ISP mass spectrum, m/e: 387.4 (M+1 calculated for $C_{22}H_{21}F_3N_2O_2$: 387).

Example 19

In analogy to example 6 there was prepared: on reaction of 2-methyl-4-pyrrolidin-1-yl-quinolin-7-ol with 2-chlorobenzyl chloride, 7-(2-chloro-benzyloxy)-2-methyl-4-pyrrolidin-1-yl-quinoline hydrochloride as a white solid. ISP mass spectrum, m/e: 353.3 (M+1 calculated for $C_{21}H_{21}ClN_2O$: 353).

Example 20

In analogy to example 6 there was prepared: on reaction of 2-methyl-4-pyrrolidin-1-yl-quinolin-7-ol with 3-chlorobenzyl chloride, 7-(3-chloro-benzyloxy)-2-methyl-4-pyrrolidin-1-yl-quinoline hydrochloride as a light-yellow solid. ISP mass spectrum, m/e: 353.3 (M+1 calculated for $C_{21}H_{21}ClN_2O$: 353).

Example 21

In analogy to example 6 there was prepared: on reaction of 2-methyl-4-pyrrolidin-1-yl-quinolin-7-ol with 4-chlorobenzyl chloride, 7-(4-chloro-benzyloxy)-2-methyl-4-pyrrolidin-1-yl-quinoline hydrochloride as an off-white solid. ISP mass spectrum, m/e: 353.3 (M+1 calculated for $C_{21}H_{21}ClN_2O$: 353).

Example 22

In analogy to example 6 there was prepared: on reaction of 2-methyl-4-pyrrolidin-1-yl-quinolin-7-ol with 3-(chloromethyl)pyridine hydrochloride, whereby the product was isolated as free base, 2-methyl-7-(pyridin-3-ylmethoxy)-4-pyrrolidin-1-yl-quinoline as a red solid. ISP mass spectrum, m/e: 320.4 (M+1 calculated for $C_{22}H_{21}N_3O$: 320).

Example 23

In analogy to example 6 there was prepared: on reaction of 2-methyl-4-pyrrolidin-1-yl-quinolin-7-ol with 3-bromomethyl benzonitrile, whereby the product was isolated as free base, 3-(2-methyl-4-pyrrolidin-1-yl-quinolin-7-yloxymethyl)-benzonitrile as a yellow solid. ISP mass spectrum, m/e: 344.4 (M+1 calculated for $C_{22}H_{21}N_3O$: 344).

Example 24

In analogy to example 6 there was prepared: on reaction of 2-methyl-4-pyrrolidin-1-yl-quinolin-7-ol with 2-bromopropane, 7-isopropoxy-2-methyl-4-pyrrolidin-1-yl-quinoline hydrochloride as a light-yellow solid. ISP mass spectrum, m/e: 271.4 (M+1 calculated for $C_{17}H_{22}N_2O$: 271).

Example 25

In analogy to example 6 there was prepared: on reaction of 2-methyl-4-pyrrolidin-1-yl-quinolin-7-ol with 1-bromo-2-methoxyethane, 7-(2-methoxy-ethoxy)-2-methyl-4-pyrrolidin-1-yl-quinoline hydrochloride as a light-brown solid. ISP mass spectrum, m/e: 287.2 (M+1 calculated for $C_{17}H_{22}N_2O_2$: 287).

Example 26

In analogy to example 6 there was prepared: on reaction of 2-methyl-4-pyrrolidin-1-yl-quinolin-7-ol with 4-(2-chloroethyl)-morpholine hydrochloride, whereby the product was isolated as free base, 2-methyl-7-(2-morpholin-4-yl-ethoxy)-4-pyrrolidin-1-yl-quinoline as a brown solid. ISP mass spectrum, m/e: 342.3 (M+1 calculated for $C_{20}H_{27}N_3O_2$: 342).

Example 27

In analogy to example 6 there was prepared: on reaction of 2-methyl-4-pyrrolidin-1-yl-quinolin-7-ol with 4-(chloromethyl)pyridine hydrochloride, 2-methyl-7-(pyridin-4-ylmethoxy)-4-pyrrolidin-1-yl-quinoline hydrochloride as a light-yellow solid. ISP mass spectrum, m/e: 320.4 (M+1 calculated for $C_{20}H_{21}N_3O$: 320).

Example 28 a) A mixture of 436 mg (1.5 mmol) of 7-Benzyloxy-4-chloro-2-methyl-quinoline, product of example 1d), and 1.75 g (15 mmol) of (S)-3-ethoxypyrrolidine, prepared according to Tetrahedron Lett., 1995, 2745, was heated at 80° C. (oil bath temperature) under an argon atmosphere for 18 h after which time the reaction was completed according to HPLC analysis. The excess (S)-3-ethoxy-pyrrolidine was distilled off, and the residue was partitioned between EtOAc and water. The layers were separated, the organic layer was washed with water then saturated NaCl solution, dried over magnesium sulphate and concentrated in vacuo. The residue was taken-up in MeOH (1 ml) diluted with diethyl ether (30 ml) and then treated dropwise at RT under stirring with 0.7 ml of 3N HCL in MeOH. The solvent was removed and the remaining salt triturated with diethyl ether, then filtered off by suction and dried in a high vacuum to give 425 mg (69.7%) of the (S)-7-benzyloxy-4-(3-ethoxy-pyrrolidin-1-yl)-2-methyl-quinoline hydrochloride as a light yellow solid. ISP mass spectrum, m/e: 363.2 (M+1 calculated for $C_{23}H_{26}N_2O_2$: 363).

Example 29

A solution of 93 mg (0.23 mmol) of (S)-7-Benzyloxy-4-(3-ethoxy-pyrrolidin-1-yl)-2-methyl-quinoline hydrochloride, product of example 28, dissolved in 7 ml of MeOH was treated with 48 mg of palladium on charcoal (10%) and then hydrogenated at RT for 1.5 h until HPLC analysis indicated the completion of the reaction. The catalyst was filtered off, washed with water, and the solution was concentrated in vacuo. The residue was triturated with n hexane/diethyl ether, the solid obtained was filtered off by suction and dried in a high vacuum to give 67 mg (90%) of (S)-4-(3-ethoxy-pyrrolidin-1-yl)-2-methyl-quinolin-7-ol hydrochloride as an off-white solid. ISP mass spectrum, m/e: 273.3 (M+1 calculated for $C_{16}H_{20}N_2O_2$: 273).

Example 30

In analogy to example 6, on reaction of (S)-4-(3-ethoxy-pyrrolidin-1-yl)-2-methyl-quinolin-7-ol hydrochloride, product of example 29, with 3-methoxybenzyl chloride there was obtained: (S)-4-(3-ethoxy-pyrrolidin-1-yl)-7-(3-methoxy-benzyloxy)-2-methyl-quinoline hydrochloride as a white solid. ISP mass spectrum, m/e: 393.3 (M+1 calculated for $C_{24}H_{28}N_2O_3$: 393).

Example 31

In analogy to example 6, on reaction of (S)-4-(3-ethoxy-pyrrolidin-1-yl)-2-methyl-quinolin-7-ol hydrochloride, product of example 29, with 4-bromomethyl benzonitrile there was obtained: (S)-4-[4-(3-ethoxy-pyrrolidin-1-yl)-2-methyl-quinolin-7-yloxymethyl]-benzonitrile hydrochloride as a yellow solid. ISP mass spectrum, m/e: 388.3 (M+1 calculated for $C_{24}H_{25}N_3O_2$: 388).

Example 32

In analogy to example 6, on reaction of (S)-4-(3-ethoxy-pyrrolidin-1-yl)-2-methyl-quinolin-7-ol hydrochloride, product of example 29, with 2-bromomethyl benzonitrile there was obtained: (S)-2-[4-(3-ethoxy-pyrrolidin-1-yl)-2-methyl-quinolin-7-yloxymethyl]-benzonitrile hydrochloride as a light-orange solid. ISP mass spectrum, m/e: 388.3 (M+1 calculated for $C_{24}H_{25}N_3O_2$: 388).

Example 33 a) A solution of 1 g (3.07 mmol) of 7-benzyloxy-6-butyl-4-chloro-quinoline hydrochloride in 2.5 ml (30.7 mmol) of pyrrolidine was heated at 60° C. with stirring under an argon atmosphere for 24 h after which time the reaction was completed according to HPLC analysis. The excess pyrrolidine was evaporated off, and the residue was partitioned between EtOAc and water. The layers were separated and the aqueous layer once extracted with AcOEt. The combined organic layers were washed with water then saturated NaCl solution, dried over magnesium sulphate and concentrated in vacuo to give 1.12 g (97.4%) of the 7-benzyloxy-6-butyl-4-pyrrolidin-1-yl-quinoline as a brown oil. ISP mass spectrum, m/e: 361.3 (M+1 calculated for $C_{24}H_{28}N_2O$: 361).

Preparation of the Starting Material:

b) A suspension of 1.75 g (5 mmol) of 7-benzyloxy-6-butyl-4-oxo-1,4-dihydro-quinoline-3-carboxylic acid (prepared from methyl benzoquate on ester hydrolysis with KOH in EtOH—$H_2O$) in 9 ml of quinoline was treated with 57 mg (0.9 mmol) of Cu powder and heated for 1 h at 200° C. The black reaction mixture was cooled to RT, 80 ml of diethyl ether were added and the solid which precipitated was filtered off by suction. It was then taken up in 100 ml of MeOH, heated to reflux and filtered hot. The filtrate was then concentrated in vacuo. The residue was triturated with diethyl ether, filtered off by suction and dried in a high vacuum to give 966 mg (63%) of the 7-benzyloxy-6-butyl-1H-quinolin-4-one as a light-yellow solid. ISP mass spectrum, m/e: 308.3 (M+1 calculated for $C_{20}H_{21}NO_2$: 308).

c) A suspension of 900 mg (2.93 mmol) of 7-benzyloxy-6-butyl-1H-quinolin-4-one in 1.44 ml of $POCl_3$ (15.8 mmol) was treated with 0.074 ml of N,N-dimethylaniline and heated at 60° C. for 3 h with stirring. The reaction mixture was then poured into ice water and stirred for 0.5 h. The solid which precipitated was filtered off by suction washed with water and dried in a high vacuum to give 1.05 g (99%) of 7-benzyloxy-6-butyl-4-chloro-quinoline hydrochloride as light gray solid. ISP mass spectrum, m/e: XX (M+1 calculated for $C_{20}H_{20}ClNO$: 325.84).

Example 34

A solution of 1.02 g (2.83 mmol) of the 7-benzyloxy-6-butyl-4-pyrrolidin-1-yl-quinoline, product of example 33, dissolved in 50 ml of MeOH was treated with 0.33 g of palladium on charcoal (10%) and then hydrogenated at RT for 2 h until TLC analysis indicated the completion of the reaction. The catalyst was filtered off, the solution was concentrated in vacuo and the residue was dried in a high vacuum to give 0.65 g (82%) of the 6-butyl-4-pyrrolidin-1-yl-quinolin-7-ol as a light yellow solid. ISP mass spectrum, m/e: 271.3 (M+1 calculated for $C_{17}H_{22}N_2O$: 271).

Example 35

In analogy to example 6, on reaction of 6-butyl-4-pyrrolidin-1-yl-quinolin-7-ol, product of example 34, with methyl iodide chloride there was obtained: 6-butyl-7-methoxy-4-pyrrolidin-1-yl-quinoline hydrochloride as a waxy brown solid. ISP mass spectrum, m/e: 285.3 (M+1 calculated for $C_{18}H_{24}N_2O$: 285).

Example 36

In analogy to example 6, on reaction of 6-butyl-4-pyrrolidin-1-yl-quinolin-7-ol, product of example 34, with ethyl iodide chloride there was obtained: 6-butyl-7-ethoxy-4-pyrrolidin-1-yl-quinoline hydrochloride as an amorphous yellow solid. ISP mass spectrum, m/e: 299.4 (M+1 calculated for $C_{19}H_{26}N_2O$: 299).

Example 37

In analogy to example 6, on reaction of 6-butyl-4-pyrrolidin-1-yl-quinolin-7-ol, product of example 34, with bromomethyl cyclopropane there was obtained: 6-butyl-7-cyclopropylmethoxy-4-pyrrolidin-1-yl-quinoline hydrochloride as an off-white solid. ISP mass spectrum, m/e: 325.3 (M+1 calculated for $C_{21}H_{28}N_2O$: 325).

Example 38

In analogy to example 6, on reaction of 6-butyl-4-pyrrolidin-1-yl-quinolin-7-ol, product of example 34, 4-bromomethyl benzonitrile there was obtained: 4-(6-butyl-4-pyrrolidin-1-yl-quinolin-7-yloxymethyl)-benzonitrile as a light yellow solid. ISP mass spectrum, m/e: 386.4 (M+1 calculated for $C_{25}H_{27}N_3O$: 386).

Example 39

A solution of 2 g (6.9 mmol) of 7-benzyloxy-4-chloro-2-methyl-quinoline, product of example 1d), in 15.5 ml (0.137 mol) of hexamethyleneimine was heated at 120° C. (oil bath temperature) with stirring under an argon atmosphere for 100 h after which time the reaction was completed according to HPLC analysis. The reaction mixture was cooled to RT and then partitioned between EtOAc and water. The layers were separated the aqueous layer once extracted with AcOEt. The combined organic layers were washed with water then saturated NaCl solution, dried over magnesium sulphate and concentrated in vacuo. The oily residue was dissolved in a small amount of MeOH and treated under stirring with 4 ml of 3N HCl in MeOH. The solvent was removed in vacuo, the residue triturated with diethyl ether under stirring for 1.5 h and the obtained solid filtered off by suction and dried in a high vacuum. (Further material was obtained on evaporation of the filtrate and treatment of the residue as described above). The desired 4-azepan-1-yl-7-benzyloxy-2-methyl-quinoline hydrochloride, 1.46 g (55.2%) was thus obtained as a light brown solid. ISP mass spectrum, m/e: 347.4 (M+1 calculated for $C_{23}H_{26}N_2O$: 347).

Example 40

A solution of 1.45 g (3.78 mmol) of 4-azepan-1-yl-7-benzyloxy-2-methyl-quinoline hydrochloride, product of example 39, dissolved in 120 ml of MeOH was treated with 700 mg of palladium on charcoal (10%) and then hydrogenated at RT for 2 h until HPLC analysis indicated the completion of the reaction. The catalyst was filtered off, washed with water, and the solution was concentrated in vacuo. The residue was triturated with diethyl ether, the solid obtained was filtered off by suction and dried in a high vacuum to give 1 g (90.4%) 4-azepan-1-yl-2-methyl-quinolin-7-ol hydrochloride as a light gray solid. ISP mass spectrum, m/e: 257.2 (M+1 calculated for $C_{16}H_{20}N_2O$: 257).

Example 41

In analogy to example 6, on reaction of 4-azepan-1-yl-2-methyl-quinolin-7-ol hydrochloride, product of example 40, with 4-(chloromethyl)pyridine hydrochloride there was obtained: 4-azepan-1-yl-2-methyl-7-(pyridin-4-ylmethoxy)-quinoline hydrochloride as a light yellow solid. ISP mass spectrum, m/e: 348.4 (M+1 calculated for $C_{22}H_{25}N_3O$: 348).

Example 42

In analogy to example 6, on reaction of 4-azepan-1-yl-2-methyl-quinolin-7-ol hydrochloride, product of example 40, with 4-bromomethyl benzonitrile there was obtained: 4-(4-azepan-1-yl-2-methyl-quinolin-7-yloxymethyl)-benzonitrile hydrochloride as a light yellow solid. ISP mass spectrum, m/e: 372.3 (M+1 calculated for $C_{24}H_{25}N_3O$: 373).

Example 43

In analogy to example 6, on reaction of 4-azepan-1-yl-2-methyl-quinolin-7-ol hydrochloride, product of example 40, with 3-bromomethyl benzonitrile there was obtained: 3-(4-azepan-1-yl-2-methyl-quinolin-7-yloxymethyl)-benzonitrile hydrochloride as a light yellow solid. ISP mass spectrum, m/e: 372.3 (M+1 calculated for $C_{24}H_{25}N_3O$: 373).

Example 44

In analogy to example 6, on reaction of 4-azepan-1-yl-2-methyl-quinolin-7-ol hydrochloride, product of example 40, with 2-(chloromethyl)pyridine hydrochloride there was obtained: 4-azepan-1-yl-2-methyl-7-(pyridin-2-ylmethoxy)-quinoline hydrochloride as a light yellow solid. ISP mass spectrum, m/e: 348.5 (M+1 calculated for $C_{22}H_{25}N_3O$: 348).

Example 45 a) A suspension of 1 g (3.5 mmol) of 6-bromo-4-chloro-7-methoxy-2-methyl-quinoline in 20 ml of EtOH was treated sequentially at RT and under stirring with 0.49 g (7 mmol) of pyrrolidine, 0.137 g (1.4 mmol) of pyridine and a catalytic amount of NaI. The mixture was then heated to reflux for 20 h, cooled to RT and concentrated in vacuo. The residue was applied to a silica gel column with $CH_2Cl_2$/

MeOH (7:1) as eluent. Combinations of the purified fractions and concentration in vacuo gave 0.85 g (68.2%) of the 6-bromo-7-methoxy-2-methyl-4-pyrrolidin-1-yl-quinoline hydrochloride as light brown solid. ISP mass spectrum, m/e: 323.3 (M+1 calculated for $C_{15}H_{17}BrN_2O$: 323).

Preparation of the Starting Material:

b) 7.66 g (37.9 mmol) of 4-bromo-3-methoxy-phenylamine (preparation described in Tetrahedron Lett., 1995, 7583) were dissolved in 80 ml of cyclohexane at 70° C. and subsequently treated under stirring with 72 mg (0.38 mmol) of p-toluenesulfonic acid monohydrate and 4.93 g (37.9 mmol) of ethyl acetoacetate. The solution was then heated at reflux for 3.5 h with a water separator funnel connected. It was then cooled to RT and concentrated in vacuo. The residue was applied to a silica gel column with hexane/diethyl ether (3:1) as eluent. Combinations of the purified fractions and concentration in vacuo gave 8.2 g (68.8%) of the (Z)-3-(4-bromo-3-methoxy-phenylamino)-but-2-enoic acid ethyl ester, as a yellow solid. ISP mass spectrum, m/e: 316.2(M+1 calculated for $C_{13}H_{16}BrNO_3$: 316).

c) A suspension of 6.6 g (21 mmol) of (Z)-3-(4-bromo-3-methoxy-phenylamino)-but-2-enoic acid ethyl ester in 40 ml of Dowtherm A were heated under stirring at 220° C. for 7.5 h after which time TLC analysis indicated completion of the reaction. The mixture was cooled to RT under stirring and the solvent was decanted off. The remaining solid residue was triturated with hexane, filtered off by suction and dried in a high vacuum to give 4.7 g (84%) of the 6-bromo-7-methoxy-2-methyl-quinolin-4-ol as a dark brown solid. EI mass spectrum, m/e: 269 (M calculated for $C_{11}H_{10}BrNO_2$: 269).

d) A suspension of 4.6 g (17.5 mmol) of 6-bromo-7-methoxy-2-methyl-quinolin-4-ol in 14.8 ml (158 mmol) of $POCl_3$ was heated at 60° C. for 20 h with stirring. It was then cooled to RT and 50 ml of diethyl ether were added. The solid that precipitated was filtered off by suction and dried in a high vacuum to give 3.85 g of the 6-bromo-4-chloro-7-methoxy-2-methyl-quinoline as a dark brown solid. EI mass spectrum, m/e: 287 (M calculated for $C_{11}H_9BrClNO$: 287).

Example 46

A solution of 115 mg (0.32 mmol) of 6-bromo-7-methoxy-2-methyl-4-pyrrolidin-1-yl-quinoline hydrochloride, compound of example 45 a), was dissolved in 5 ml of dry $CH_2Cl_2$ under an argon atmosphere and treated dropwise with 0.16 g (0.64 mmol) of 1M $BBr_3$ in $CH_2Cl_2$ with ice cooling. After 0.5 h the ice bath was removed, the solution was stirred for 2 h at RT and then heated to reflux for 12 h. The reaction mixture was cooled to RT and partitioned between ice water and $CH_2Cl_2$. The layers were separated, the aqueous layer further extracted with CHCl2/MeOH mixtures (8:1).

The combined organic layers were dried over magnesium sulphate and concentrated in vacuo. The residue was applied to a silica gel column with $CH_2Cl_2$/MeOH (15:1) as eluent. Combinations of the purified fractions and concentration in vacuo gave 39 mg (35%) of the 6-bromo-2-methyl-4-pyrrolidin-1-yl-quinolin-7-ol hydrochloride as a light brown solid. ISP mass spectrum, m/e: 307.2 (M+1 calculated for $C_{14}H_{15}BrN_2O$: 307).

Example 47

In analogy to example 6, on reaction 6-bromo-2-methyl-4-pyrrolidin-1-yl-quinolin-7-ol hydrochloride, product of example 46, with 4-bromomethyl benzonitrile there was obtained: 4-(6-bromo-2-methyl-4-pyrrolidin-1-yl-quinolin-7-yloxymethyl)-benzonitrile as a light yellow solid. ISP mass spectrum, m/e: 424.3 (M+1 calculated for $C_{22}H_{20}BrN_3O$: 424).

Example 48 a) A solution of 319 mg (0.92 mmol) of 4-chloro-7-methoxy-quinolin-2-ylamine in 20 ml of isopropanol was treated with 130 mg (1.83 mmol) of pyrrolidine and heated at 60° C. for 6 h. The reaction mixture was cooled to RT, concentrated in vacuo. The residue was applied to a silica gel column with hexane/AcOEt (1:1) as eluent. The purified fractions were combined and concentrated in vacuo upon which the desired product crystallized out. The crystals were filtered off and dried in a high vacuum to give 48 mg (21%) of 7-methoxy-4-pyrrolidin-1-yl-quinolin-2-ylamine hydrochloride as a light brown solid. EI mass spectrum, m/e: 243.2 (M calculated for $C_{14}H_{17}N_3O$: 243).

b) Above used starting material was obtained from commercially available 1-(4-chloro-7-methoxy-2-quinolyl)-3-phenylurea (500 mg, 1.53 mmol) on heating in a solution of isopropanol/THF/$CH_2Cl_2$ (30 ml:20 ml:20 ml) and in the presence of 217 mg (3 mmol) of pyrrolidine for 12 h at 60° C. Upon concentration of the reaction mixture the desired product crystallized out. It was filtered off by suction and dried in a high vacuum to give 250 mg (78%) of the 4-chloro-7-methoxy-quinolin-2-ylamine as a light brown solid. ISP mass spectrum, m/e: 208.1 (M calculated for $C_{10}H_9ClN_2O$: 208).

Example 49

In analogy to example 45 a), from 4-chloro-7-methoxyquinoline (synthesis described in: J. Med. Chem., 1998, 4918) and pyrrolidine there was obtained: 7-methoxy-4-pyrrolidin-1-yl-quinoline hydrochloride as a yellow solid. ISP mass spectrum, m/e: 229.2 (M+1 calculated for $C_{14}H_{16}N_2O$: 229).

Example 50

In analogy to example 46, from 7-methoxy-4-pyrrolidin-1-yl-quinoline hydrochloride and on treatment with $BBr_3$ in toluene under reflux there was obtained was obtained: 4-pyrrolidin-1-yl-quinolin-7-ol as a brown solid. ISP mass spectrum, m/e: 215.3 (M+1 calculated for $C_{13}H_{14}N_2O$: 215).

Example 51

In analogy to example 6 there was prepared: on reaction of 2-methyl-4-pyrrolidin-1-yl-quinolin-7-ol with 3,5-dimethoxybenzyl chloride, 7-(3,5-dimethoxy-benzyloxy)-2-methyl-4-pyrrolidin-1-yl-quinoline hydrochloride as a light yellow solid. ISP mass spectrum, m/e: 379.4 (M+1 calculated for $C_{23}H_{26}N_2O_3$: 379).

Example 52

In analogy to example 6 there was prepared: on reaction of 2-methyl-4-pyrrolidin-1-yl-quinolin-7-ol with 3,4-dimethoxybenzyl chloride, whereby the product was isolated as free base; 7-(3,4-dimethoxy-benzyloxy)-2-methyl-4-pyrrolidin-1-yl-quinoline as a light yellow solid. ISP mass spectrum) m/e: 379.4 (M+1 calculated for $C_{23}H_{26}N_2O_3$: 379).

Example 53

In analogy to example 6 there was prepared: on reaction of 2-methyl-4-pyrrolidin-1-yl-quinolin-7-ol with ethyl iodide, whereby the product was isolated as free base, 7-ethoxy-2-methyl-4-pyrrolidin-1-yl-quinoline as a brown solid. ISP mass spectrum, m/e: 257.1 (M+1 calculated for $C_{16}H_{20}N_2O$: 257).

Example 54

In analogy to example 6 there was prepared: on reaction of 2-methyl-4-pyrrolidin-1-yl-quinolin-7-ol with 6-methyl-2-chloromethyl-pyridine, 2-Methyl-7-(6-methyl-pyridin-3-ylmethoxy)-4-pyrrolidin-1-yl-quinoline hydrochloride as off-white solid. ISP mass spectrum, m/e: 334.3 (M+1 calculated for $C_{21}H_{23}N_3O$: 334).

Example 55

In analogy to example 6 there was prepared: on reaction of 2-methyl-4-pyrrolidin-1-yl-quinolin-7-ol with 2-methyl-3-chloromethyl-pyridine, 2-methyl-7-(2-methyl-pyridin-3-ylmethoxy)-4-pyrrolidin-1-yl-quinoline hydrochloride as light yellow solid. ISP mass spectrum, m/e: 334.3 (M+1 calculated for $C_{21}H_{23}N_3O$: 334).

Example 56

In analogy to example 6 there was prepared: on reaction of 2-methyl-4-pyrrolidin-1-yl-quinolin-7-ol with 6-chloro-3-chloromethyl-pyridine, 7-(6-chloro-pyridin-3-ylmethoxy)-2-methyl-4-pyrrolidin-1-yl-quinoline hydrochloride as white solid. ISP mass spectrum, m/e: 354.2 (M+1 calculated for $C_{20}H_{20}ClN_3O$: 354).

Example 57

In analogy to example 6 there was prepared: on reaction of 2-methyl-4-pyrrolidin-1-yl-quinolin-7-ol with 2-chloro-3-chloromethyl-pyridine, 7-(2-chloro-pyridin-3-ylmethoxy)-2-methyl-4-pyrrolidin-1-yl-quinoline hydrochloride as white solid. ISP mass spectrum, m/e: 354.3 (M+1 calculated for $C_{20}H_{20}ClN_3O$: 354).

Example 58

In analogy to example 6 there was prepared: on reaction of 2-methyl-4-pyrrolidin-1-yl-quinolin-7-ol with 3-chloromethyl-2-fluoro-pyridine, 7-(2-fluoro-pyridin-3-ylmethoxy)-2-methyl-4-pyrrolidin-1-yl-quinoline hydrochloride as white solid. ISP mass spectrum, m/e: 338.2 (M+1 calculated for $C_{20}H_{20}FN_3O$: 338).

Example 59

In analogy to example 6 there was prepared: on reaction of 2-methyl-4-pyrrolidin-1-yl-quinolin-7-ol with 2-chloro-3-chloromethyl-6-methyl-pyridine, 7-(2-chloro-6-methyl-pyridin-3-ylmethoxy)-2-methyl-4-pyrrolidin-1-yl-quinoline hydrochloride as light yellow solid. ISP mass spectrum, m/e: 368.2 (M+1 calculated for $C_{21}H_{22}ClN_3O$: 368).

Example 60

In analogy to example 6 there was prepared: on reaction of 2-methyl-4-pyrrolidin-1-yl-quinolin-7-ol with 3-bromomethyl-2-chloro-6-trifluoromethyl-pyridine, whereby the product was isolated as free base, 7-(2-chloro-6-trifluoromethyl-pyridin-3-ylmethoxy)-2-methyl-4-pyrrolidin-1-yl-quinoline as a white solid. ISP mass spectrum, m/e: 422.2 (M+1 calculated for $C_{21}H_{19}ClF_3N_3O$: 422).

Example 61

In analogy to example 6 there was prepared: on reaction of 2-methyl-4-pyrrolidin-1-yl-quinolin-7-ol with 5-chloromethyl-pyridine-2-carbonitrile, 5-(2-methyl-4-pyrrolidin-1-yl-quinolin-7-yloxymethyl)-pyridine-2-carbonitrile hydrochloride as light yellow solid. ISP mass spectrum, m/e: 345.4 (M+1 calculated for $C_{21}H_{20}N_4O$: 345).

Example 62

In analogy to example 6 there was prepared: on reaction of 2-methyl-4-pyrrolidin-1-yl-quinolin-7-ol with 2-chloro-5-chloromethyl-thiophene, 7-(5-chloro-thiophen-2-ylmethoxy)-2-methyl-4-pyrrolidin-1-yl-quinoline hydrochloride as white solid. ISP mass spectrum, m/e: 359.2 (M+1 calculated for $C_{19}H_{19}ClN_2OS$: 359).

Example 63

In analogy to example 6 there was prepared: on reaction of 2-methyl-4-pyrrolidin-1-yl-quinolin-7-ol with 3-chloromethyl-thiophene, 2-methyl-4-pyrrolidin-1-yl-7-(thiophen-3-ylmethoxy)-quinoline hydrochloride as white solid. ISP mass spectrum, m/e: 325.4 (M+1 calculated for $C_{19}H_{20}N_2OS$: 325).

Example 64

In analogy to example 6 there was prepared: on reaction of 2-methyl-4-pyrrolidin-1-yl-quinolin-7-ol with 4-bromobenzonitrile, whereby the product was isolated as free base, 4-(2-methyl-4-pyrrolidin-1-yl-quinolin-7-yloxy)-benzonitrile as a white solid. ISP mass spectrum, m/e 330.5 (M+1 calculated for $C_{21}H_{19}N_3O$: 330).

Example 65

In analogy to example 6, on reaction of (S)-4-(3-ethoxy-pyrrolidin-1-yl)-2-methyl-quinolin-7-ol hydrochloride, product of example 29, with 3-chloromethyl-2-fluoro-pyridine hydrochloride there was obtained: (S) 4-(3-ethoxy-pyrrolidin-1-yl)-7-(2-fluoro-pyridin-3-ylmethoxy)-2-methyl-quinoline hydrochloride as a white solid. ISP mass spectrum, m/e: 382.4 (M+1 calculated for $C_{22}H_{24}FN_3O_2$: 382).

Example 66

In analogy to example 6, on reaction of (S)-4-(3-ethoxy-pyrrolidin-1-yl)-2-methyl-quinolin-7-ol hydrochloride, product of example 29, with 2-chloro-3-chloromethyl-pyridine hydrochloride there was obtained: (S) 7-(2-chloro-pyridin-3-ylmethoxy)-4-(3-ethoxy-pyrrolidin-1-yl)-2-methyl-quinoline hydrochloride as a light yellow solid. ISP mass spectrum, m/e: 398.4 (M+1 calculated for $C_{22}H_{24}ClN_3O_2$: 398).

Example 67

In analogy to example 6, on reaction of (S)-4-(3-ethoxy-pyrrolidin-1-yl)-2-methyl-quinolin-7-ol hydrochloride, product of example 29, with 3-chloromethyl-pyridine hydrochloride there was obtained: (S) 4-(3-ethoxy-pyrrolidin-1-yl)-2-methyl-7-(pyridin-3-ylmethoxy)-quinoline hydrochloride as a light brown solid. ISP mass spectrum, m/e: 364.3 (M+1 calculated for $C_{22}H_{25}N_3O_2$: 364).

Example 68

In analogy to example 6, on reaction of (S)-4-(3-ethoxy-pyrrolidin-1-yl)-2-methyl-quinolin-7-ol hydrochloride, product of example 29, with 5-chloromethyl-pyridine-2-carbonitrile there was obtained: (S) 5-[4-(3-ethoxy-pyrrolidin-1-yl)-2-methyl-quinolin-7-yloxymethyl]-

Example 69

In analogy to example 6, on reaction of 4-azepan-1-yl-2-methyl-quinolin-7-ol hydrochloride, product of example 40, with 3-methoxybenzyl chloride there was obtained: 4-azepan-1-yl-7-(3-methoxy-benzyloxy)-2-methyl-quinoline hydrochloride as a light yellow solid. ISP mass spectrum, m/e: 377.4 (M+1 calculated for $C_{24}H_{28}N_2O_2$: 377).

Example 70

In analogy to example 6, on reaction of 4-azepan-1-yl-2-methyl-quinolin-7-ol hydrochloride, product of example 40, with 2-bromomethyl-benzonitrile there was obtained: 2-(4-azepan-1-yl-2-methyl-quinolin-7-yloxymethyl)-benzonitrile hydrochloride as an off-white solid. ISP mass spectrum, m/e: 372.3 (M+1 calculated for $C_{24}H_{25}N_3O$: 372).

Example 71

In analogy to example 6, on reaction of 4-azepan-1-yl-2-methyl-quinolin-7-ol hydrochloride, product of example 40, with 3-chlorobenzyl chloride there was obtained: 4-azepan-1-yl-7-(3-chloro-benzyloxy)-2-methyl-quinoline hydrochloride as a light yellow solid. ISP mass spectrum, m/e: 381.3 (M+1 calculated for $C_{23}H_{25}ClN_2O$: 381).

Example 72

In analogy to example 6, on reaction of 4-azepan-1-yl-2-methyl-quinolin-7-ol hydrochloride, product of example 40, with 4-chlorobenzyl chloride there was obtained: 4-Azepan-1-yl-7-(4-chloro-benzyloxy)-2-methyl-quinoline hydrochloride as a light yellow solid. ISP mass spectrum, m/e: 381.3 (M+1 calculated for $C_{23}H_{25}ClN_2O$: 381).

Example 73

A suspension of 98.5 mg (0.25 mmol) of 7-(6-chloro-pyridin-3-ylmethoxy)-2-methyl-4-pyrrolidin-1-yl-quinoline hydrochloride, product of example 56, in 0.44 ml (5 mmol) of morpholine was heated under nitrogen at 60° C. (oil bath temperature) for 23 h and further 72 h at 100° C. The mixture was cooled to RT and partitioned between EtOAc and water. The organic layer was separated, washed with water, dried over magnesium acetate and concentrated in vacuo. The residue was taken up in ether (20 ml), insoluble material was removed by filtration and the filtrate treated with 0.1 ml of 3 N HCl in MeOH. The solid that precipitated was collected, triturated with ether (5 ml), filtered off by suction, dried in a high vacuum and then applied to a to silica gel column with $CH_2Cl_2$/MeOH/$NH_4OH$ (19:1:0.05) as eluent. The purified fractions were combined and concentrated in vacuo to a small volume then acidified by adding a few drops of 3 N HCl in MeOH. The solvent was taken off in vacuo to give 23 mg (18%) of the desired 2-methyl-7-(6-morpholin-4-yl-pyridin-3-ylmethoxy)-4-pyrrolidin-1-yl-quinoline hydrochloride as a light yellow solid. ISP mass spectrum, m/e: 405.5 (M+1 calculated for $C_{24}H_{28}N_4O_2$: 405).

Example 74

A suspension of 98.5 mg (0.25 mmol) of 7-(6-chloro-pyridin-3-ylmethoxy)-2-methyl-4-pyrrolidin-1-yl-quinoline hydrochloride, product of example 56, 16 mg (0.03 mmol) of BINAP, 2.8 mg (0.01 mmol) of Pd(II) acetate, and 99 mg (1 mmol) of sodium tert-butylate in toluene (4.5 ml) was treated at RT with 36 mg (0.5 mmol) of pyrrolidine and then heated at reflux under an argon atmosphere for 4 h. The reaction mixture was cooled to RT, diluted with methylene chloride (10 ml), and then filtered. The filtrate was concentrated in vacuo, the residue triturated with ether, filtered off by suction and dried in a high vacuum to give 88 mg (84%) of the 2-methyl-4-pyrrolidin-1-yl-7-(6-pyrrolidin-1-yl-pyridin-3-ylmethoxy)-quinoline as a white solid. ISP mass spectrum, m/e: 389.3 (M+1 calculated for $C_{24}H_{28}N_4O$: 389).

Example 75

A suspension of 114 mg (0.5 mmol) of 2-methyl-4-pyrrolidin-1-yl-quinolin-7-ol, product of example 2, 71 mg (0.53 mmol) of 3-dimethylamino-2,2-dimethyl-1-propanol, 196.7 mg (0.75 mmol) of triphenyl phosphine in THF (4 ml) was treated at RT with 123 $\mu$l (0.75 mmol) of diethyl azodicarboxylate and stirred at RT for 48 h. The precipitate that had formed was removed by filtration, the filtrate was concentrated in vacuo and the oily residue obtained was applied to silica gel column with $CH_2Cl_2$/MeOH/$NH_4OH$ (90:10:1) as eluent. The purified fractions were combined and concentrated in vacuo. The residue was taken up in ether, the crystalline solid that formed was filtered off by suction and dried in a high vacuum to give 24 mg (23%) of the desired [2,2-dimethyl-3-(2-methyl-4-pyrrolidin-1-yl-quinolin-7-yloxy)-propyl]-dimethyl-amine as an off-white solid. ISP mass spectrum, m/e: 342.4 (M+1 calculated for $C_{21}H_{31}N_3O$: 342). (Further material, 30 mg, 29%, was obtained on concentration of the mother liquid and collection of the product as hydrochloride salt).

Example 76

In analogy to example 75, on reaction of 2-methyl-4-pyrrolidin-1-yl-quinolin-7-ol, with 4-hydroxy-1-methylpiperidine there was obtained: 2-methyl-7-(1-methyl-piperidin-4-yloxy)-4-pyrrolidin-1-yl-quinoline as a yellow solid. ISP mass spectrum, m/e: 326.5 (M+1 calculated for $C_{20}H_{27}N_3O$: 326).

Example 77

In analogy to example 75, on reaction of 2-methyl-4-pyrrolidin-1-yl-quinolin-7-ol, with 3-hydroxy-tetrahydrofurane there was obtained: 2-methyl-4-pyrrolidin-1-yl-7-(tetrahydro-furan-3-yloxy)-quinoline as a light yellow solid. ISP mass spectrum, m/e: 299.4 (M+1 calculated for $C_{18}H_{22}N_2O_2$: 299).

Example 78

In analogy to example 75, on reaction of 2-methyl-4-pyrrolidin-1-yl-quinolin-7-ol, with (1-methyl-piperidin-4-yl)-methanol, and on isolation of the product as hydrochloride, there was obtained: 2-Methyl-7-(1-methyl-piperidin-4-ylmethoxy)-4-pyrrolidin-1-yl-quinoline hydrochloride as a white solid. ISP mass spectrum, m/e: 340.3 (M+1 calculated for $C_{21}H_{29}N_3O$: 340).

Example 79

In analogy to example 75, on reaction of 2-methyl-4-pyrrolidin-1-yl-quinolin-7-ol, with 3-morpholin-4-yl-propan-1-ol, and on isolation of the product as hydrochloride, there was obtained: 2-methyl-7-(3-morpholin-4-yl-propoxy)-4-pyrrolidin-1-yl-quinoline hydrochloride as an off-white solid. ISP mass spectrum, m/e: 356.4 (M+1 calculated for $C_{21}H_{29}N_3O_2$: 356).

Example 80

To a cooled (0° C.) solution of 2-methyl-4-pyrrolidin-1-yl-quinolin-7-ol (797 mg, 3.49 mmol) in dimethylformamide (13 mL) was added sodium hydride (ca. 60% in oil, 168 mg, 4.19 mmol). After 30 min at 0° C., ethyl bromoacetate (0.5 mL, 4.50 mmol) was injected. After 2 h30, an aqueous solution of $NaHCO_3$ was added and the aqueous layer was extracted with dichloromethane. The combined organic phases were washed with brine and water and then dried over sodium sulfate. After filtration, solvents were removed in a high vacuum. The brown oil was triturated with diethylether. After filtration, the solid was dried in a high vacuum to give 660 g (60.2%) of (2-methyl-4-pyrrolidin-1-yl-quinolin-7-yloxy)-acetic acid ethyl ester as a light brown solid. ISP mass spectrum, m/e: 315.4 (M+1 calculated for $C_{18}H_{22}N_2O_3$: 315.4).

Example 81

To a cooled (0° C.) solution of (2-methyl-4-pyrrolidin-1-yl-quinolin-7-yloxy)-acetic acid ethyl ester (613 mg, 1.95 mmol) in ethyl alcohol (10 mL) was added sodium borohydride (506 mg, 12.84 mmol). The mixture was stirred 7 h at room temperature. Aqueous hydrochloride was added carefully (12M, 1 mL). The suspension was filtered and the solid was washed with MeOH. The solution was dried over sodium sulfate, filtered and the solvent was removed in a high vacuum to give 425 mg (80.0%) of 2-(2-methyl-4-pyrrolidin-1-yl-quinolin-7-yloxy)-ethanol as a brown oil. ISP mass spectrum, m/e: 273.4 (M+1 calculated for $C_{16}H_{20}N_2O_2$: 273.4).

Example 82

To a cooled (0° C.) solution of of 2-(2-methyl-4-pyrrolidin-1-yl-quinolin-7-yloxy)-ethanol (425 mg, 1.56 mmol) in dichloromethane (20 mL) was added triethylamine (0.9 mL, 6.49 mmol) and tosyl chloride (1115 mg, 5.85 mmol). The reaction mixture was stirred 22 h at room temperature. An aqueous solution of NaHCO3 was added. After separation, the organic layer was washed with brine. The brown gum was triturated with diethylether. After filtration, the solid was dried in a high vacuum to give 520 mg (78.1%) of toluene-4-sulfonic acid 2-(2-methyl-4-pyrrolidin-1-yl-quinolin-7-yloxy)-ethyl ester as a light yellow solid. ISP mass spectrum, m/e: 427.5 (M+1 calculated for $C_{23}H_{26}N_2O_4S$: 427.5).

Example 83

In analogy to example 6 there was prepared: on reaction of 2-methyl-4-pyrrolidin-1-yl-quinolin-7-ol with 1-(2-pyridyl)-3-chloropropane, there was obtained: 2-methyl-7-(3-pyridin-2-yl-propoxy)-4-pyrrolidin-1-yl-quinoline as a yellow viscous oil. ISP mass spectrum, m/e348.5 (M+1 calculated for $C_{22}H_{25}N_3O$: 348.5).

Example 84

In analogy to example 1, on reaction of 7-benzyloxy-4-chloro-2-methyl-quinoline with morpholine, there was obtained: 7-benzyloxy-2-methyl-4-morpholin-4-yl-quinoline as a waxy yellow solid. ISP mass spectrum, m/e: 335.3 (M+1 calculated for $C_{21}H_{22}N_2O_2$: 335).

Example 85

In analogy to example 1, on reaction of 7-benzyloxy-4-chloro-2-methyl-quinoline, with an excess of (S)-3-hydroxypyrrolidine (2,5 mole-equivalents) in 1-methyl-2-pyrrolidone as solvent at 100° C., there was obtained: (S)-1-(7-benzyloxy-2-methyl-quinolin-4-yl)-pyrrolidin-3-ol as a light brown solid. ISP mass spectrum, m/e: 335.4 (M+1 calculated for $C_{21}H_{22}N_2O_2$: 335).

Example 86

In analogy to example 1, on reaction of 7-benzyloxy-4-chloro-2-methyl-quinoline, with an excess of (R)-3-hydroxypyrrolidine (2,5 mole-equivalents) in 1-methyl-2-pyrrolidone as solvent at 100° C., there was obtained: (R)-1-(7-benzyloxy-2-methyl-quinolin-4-yl)-pyrrolidin-3-ol as a light brown solid. ISP mass spectrum, m/e: 335.3 (M+1 calculated for $C_{21}H_{22}N_2O_2$: 335).

Example 87

In analogy to example 1, on reaction of 7-benzyloxy-4-chloro-2-methyl-quinoline, with an excess of (S)-2-(hydroxymethyl)pyrrolidine (2,5 mole-equivalents) in 1-methyl-2-pyrrolidone as solvent at 100° C., there was obtained: (S)-[1-(7-benzyloxy-2-methyl-quinolin-4-yl)-pyrrolidin-2-yl]-methanol as an off-white solid. ISP mass spectrum, m/e: 349.5 (M+1 calculated for $C_{22}H_{24}N_2O_2$: 349).

Example 88

In analogy to example 1, on reaction of 7-benzyloxy-4-chloro-2-methyl-quinoline, with an excess of (S)-2-(methoxymethyl)pyrrolidine (2,5 mole-equivalents) in 1-methyl-2-pyrrolidone as solvent at 100° C., there was obtained: (S)-7-benzyloxy-4-(2-methoxymethyl-pyrrolidin-1-yl)-2-methyl-quinoline as an orange viscous oil. ISP mass spectrum, m/e: 363.2 (M+1 calculated for $C_{23}H_{26}N_2O_2$: 363).

Example 89

In analogy to example 2, on hydrogenation of (S)-7-benzyloxy-4-(2-methoxymethyl-pyrrolidin-1-yl)-2-methyl-quinoline, product of example 88, with Pd on charcoal (10%) in MeOH, there was obtained: (S)-4-(2-Methoxymethyl-pyrrolidin-1-yl)-2-methyl-quinolin-7-ol as a yellow solid. ISP mass spectrum, m/e: 273.2 (M+1 calculated for $C_{16}H_{20}N_2O_2$: 273).

Example 90

In analogy to example 6, on reaction of (S)-4-(2-Methoxymethyl-pyrrolidin-1-yl)-2 methyl-quinolin-7-ol, product of example 89, with 2-chloro-3-chloromethyl-pyridine hydrochloride there was obtained: (S)-7-(2-chloro-pyridin-3-ylmethoxy)-4-(2-methoxymethyl-pyrrolidin-1-yl)-2-methyl-quinoline hydrochloride as a light yellow solid. ISP mass spectrum, m/e: 398.4 (M+1 calculated for $C_{22}H_{24}ClN_3O_2$: 398).

Example 91

In analogy to example 6, on reaction of (S)-4-(2-Methoxymethyl-pyrrolidin-1-yl)-2-methyl-quinolin-7-ol, product of example 89, with 2-fluoro-3-chloromethyl-pyridine hydrochloride there was obtained: (S)-7-(2-fluoro-pyridin-3-ylmethoxy)-4-(2-methoxymethyl-pyrrolidin-1-yl)-2-methyl-quinoline hydrochloride as a light yellow solid. ISP mass spectrum, m/e: 382.4 (M+1 calculated for $C_{22}H_{24}FN_3O_2$: 382).

Example 92

In analogy to example 6, on reaction of (S)-4-(2-methoxymethyl-pyrrolidin-1-yl)-2-methyl-quinolin-7-ol, product of example 89, with cyclopropylmethyl bromide hydrochloride there was obtained: (S)-7-cyclopropylmethoxy-4-(2-methoxymethyl-pyrrolidin-1-yl)-2-methyl-quinoline hydrochloride as a light yellow solid. ISP mass spectrum, m/e: 327.4 (M+1 calculated for $C_{22}H_{26}N_2O_2$: 327).

Example 93

In analogy to example 2, on hydrogenation of (S)-[1-(7-benzyloxy-2-methyl-quinolin-4-yl)-pyrrolidin-2-yl]-methanol, product of example 87, with Pd on charcoal (10%) in MeOH, there was obtained: (S)-4-(2-hydroxymethyl-pyrrolidin-1-yl)-2-methyl-quinolin-7-ol as a yellow solid. ISP mass spectrum, m/e: 259.3 (M+1 calculated for $C_{15}H_{18}N_2O_2$: 259).

Example 94

In analogy to example 6, on reaction of (S)-4-(2-hydroxymethyl-pyrrolidin-1-yl)-2-methyl-quinolin-7-ol, product of example 93, with 2-fluoro-3-chloromethyl-pyridine hydrochloride there was obtained: (S)-{1-[7-(2-fluoro-pyridin-3-ylmethoxy)-2-methyl-quinolin-4-yl]-pyrrolidin-2-yl}-methanol as a light yellow solid. ISP mass spectrum, m/e: 368.4 (M+1 calculated for $C_{21}H_{22}FN_3O_2$: 368).

Example 95

In analogy to example 6, on reaction of (S)-4-(2-hydroxymethyl-pyrrolidin-1-yl)-2-methyl-quinolin-7-ol, product of example 93, with 2-chloro-3-chloromethyl-pyridine hydrochloride there was obtained: (S)-{1-[7-(2-chloro-pyridin-3-ylmethoxy)-2-methyl-quinolin-4-yl]-pyrrolidin-2-yl}-methanol as a light yellow solid. ISP mass spectrum, m/e: 384.3 M+1 calculated for $C_{21}H_{22}ClN_3O_2$: 384).

Example 96

In analogy to example 6, on reaction of (S)-4-(2-hydroxymethyl-pyrrolidin-1-yl)-2-methyl-quinolin-7-ol, product of example 93, with 2-bromomethyl-benzonitrile there was obtained: (S)-2-[4-(2-hydroxymethyl-pyrrolidin-1-yl)-2-methyl-quinolin-7-yloxymethyl]-benzonitrile as an off-white solid. ISP mass spectrum, m/e: 374.5 (M+1 calculated for $C_{23}H_{23}N_3O_2$: 374).

Example 97

In analogy to example 6, on reaction of (S)-4-(2-hydroxymethyl-pyrrolidin-1-yl)-2-methyl-quinolin-7-ol, product of example 93, with 3-chlormethyl-pyridine there was obtained: (S)-{1-[2-methyl-7-(pyridin-3-ylmethoxy)-quinolin-4-yl]-pyrrolidin-2-yl}-methanol as an light yellow solid. ISP mass spectrum, m/e: 350.5 (M+1 calculated for $C_{21}H_{23}N_3O_2$: 350).

Example 98

In analogy to example 6, on reaction of (S)-4-(2-hydroxymethyl-pyrrolidin-1-yl)-2-methyl-quinolin-7-ol, product of example 93, with 5-chloromethyl-pyridin-2-carbonitrile there was obtained: (S)-5-[4-(2-hydroxymethyl-pyrrolidin-1-yl)-2-methyl-quinolin-7-yloxymethyl]-pyridine-2-carbonitrile as an light yellow solid. ISP mass spectrum, m/e: 375.3 (M+1 calculated for $C_{22}H_{22}N_4O_2$: 375).

Example 99 a) A mixture of 3.1 g of (10.9 mmol) of 7-benzyloxy-4-chloro-6-fluoro-2-methyl-quinoline and 18.1 ml (21.8 mmol) pyrrolidine was heated at 80° C. (oil bath temperature) under an argon atmosphere for 6 h. The reaction mixture was concentrated in vacuo, the residue taken up in methylene chloride, which was washed with water, saturated NaCl solution and then dried over magnesium sulphate. The solvent was removed in vacuo, the residue purified by flash chromatography on silica gel with $CH_2Cl_2$/MeOH (100:0 to 90:10 over 1 h) as eluent. Combination of the purified fractions and concentration in vacuo gave 1.7 g (46.2%) of the 7-benzyloxy-6-fluoro-2-methyl-4-pyrrolidin-1-yl-quinoline as a brown crystalline solid. ISP mass spectrum, m/e: 337.4 (M+1 calculated for $C_{21}H_{21}FN_2O$: 337).

Preparation of the Starting Material:

b) A solution of 50 g (0.354 mol) of 4-fluoro-3-methoxy-aniline dissolved in methylene chloride (1800 ml) was treated under argon with 163.2 g (0.44 mol) of tetrabutyl-ammonium iodide, cooled to −75° C. and the treated over a period of 25 minutes with 860 ml of 1 M $BCl_3$ in methylene chloride while keeping the reaction solution between −75° C. and −64° C. The solution was stirred for 15 minutes the cooling bath was removed and stirring was continued for 24 h under argon. The reaction solution was poured into ice water (6 l) with stirring, the layers were separated, the water layer twice extracted with methylene chloride (each 1.5 l). The combined organic layers were washed twice with water (each 2 l) and discarded. The combined aqueous layers were made basic with solid $NaHCO_3$, saturated with NaCl, extracted 3 times with 2.5 l of ether and twice with 1.5 l of AcOEt. The combined organic layers were tried over magnesium sulphate and concentrated in vacuo to give 43.9 g (87.8%) of 4-fluoro-3-hydroxy-aniline as light brown crystalline solid. Melting point: 156–157° C.

c) 79 g (0.62 mol) of 4-fluoro-3-hydroxy-aniline in DMF (1.3 l) were treated under argon portion wise over a period of 15 minutes with 76.7 g (0.68 mol) of potassium t-butylate whereas the temperature of the reaction solution was kept between RT and 28° C. Stirring was continued for 15 minutes then 79 ml (0.68 mol) of benzyl chloride were added dropwise while keeping the temperature of the reaction solution between RT and 30° C. After stirring for 2 h at RT the reaction solution was poured into ice water (6 l) which was then extracted 3-fold with ether (about 3 l each). The combined organic layers were washed with brine (1.5 l) and dried over magnesium sulfate and the solvent removed in vacuo. The residue was purified by chromatography over a short silica gel column with methylene chloride as eluent. Combination of the purified fractions and concentration in vacuo gave 92.7 g (68.6%) of the desired 3-benzyloxy-4-fluoro-phenylamine as light yellow crystalline solid. ISP mass spectrum, m/e: 218.2 (M+1 calculated for $C_{13}H_{12}FNO$: 218.2).

d) 92.7 g (0.43 mol) of 3-Benzyloxy-4-fluoro-phenylamine, 57 ml (0.45 mol) of ethyl acetoacetate and 0.81 g (4 mmol) of p-toluenesulfonic acid monohydrate in 370 ml of cyclohexane were heated at reflux for 3 h in the presence of a water separator funnel. The reaction mixture was cooled to RT, ACOEt (1 l) and saturated aqueous $NaHCO_3$ solution (0.5 l) were added, the layers were separated and the organic layer once extracted with AcOEt (0.3 l). The combined organic layers were dried over magnesium sulfate and concentrated in vacuo to give 140 g (100%) of the desired 3-(3-benzyloxy-4-fluoro-phenylamino)-but-2-enoic acid ethyl ester as yellow-orange crystalline solid. Melting point: 79° C.–80° C.

e) 70.35 g (0.21 mol) of 3-(3-benzyloxy-4-fluoro-phenylamino)-but-2-enoic acid ethyl ester in Dowtherm A (220 ml) were added dropwise under argon to 400 ml of Dowtherm A heated at 250° C. (metal bath temperature). The solution was stirred further 15 minutes at 250° C. (bath temperature), cooled to RT and n-hexane was added with stirring whereby a light brown solid formed that was collected by filtration and washed with 4-times with n-hexane. The solid was then triturated with ether, collected by suction, washed 3-times with ether and then dried in a high vacuum, to give 33.9 g (57%) of the desired 7-benzyloxy-6-fluoro-2-methyl-1H-quinolin-4-one as a light brown solid. ISP mass spectrum, m/e: 284.1 (M+1 calculated for $C_{17}H_{14}FNO_2$: 284).

f) 67.8 g (0.239 mol) of 7-benzyloxy-6-fluoro-2-methyl-1H-quinolin-4-one in 220 ml (2.39 mol) of $POCl_3$ were heated at reflux for 90 minutes. The reaction mixture was cooled to RT and the solvent was removed in vacuo. The residue was partitioned between ice water (1.5 l) and methylene chloride (1 l), and 250 ml of concentrated ammonia were added slowly with stirring to adjust the aqueous layer to pH 9. The layers were separated, the aqueous layer twice extracted with methylene chloride (each 500 ml), the combined organic layers were washed with brine, dried over magnesium sulfate and then concentrated in vacuo, to give 71.5 g (86.83%) of the desired of 7-benzyloxy-4-chloro-6-fluoro-2-methyl-quinoline as an off white solid. Melting point: 110° C.–111° C.

Example 100

A solution of 1.5 g (4.46 mmol) of 7-benzyloxy-6-fluoro-2-methyl-4-pyrrolidin-1-yl-quinoline, product of example 99, dissolved in 40 ml of MeOH was treated with 0.375 g of palladium on charcoal (10%) and then hydrogenated at RT for 1.5 h until HPLC analysis indicated the completion of the reaction. The catalyst was filtered off, and the solution was concentrated in vacuo. The residue was triturated with AcOEt, collected by filtration and dried in a high vacuum to give 1.02 g (92.8%) 6-fluoro-2-methyl-4-pyrrolidin-1-yl-quinolin-7-ol as an yellow solid. ISP mass spectrum, m/e: 247.3 (M+1 calculated for $C_{14}H_{15}FN_2O$: 247).

Example 101

In analogy to example 6 there was prepared: on reaction of 6-fluoro-2-methyl-4-pyrrolidin-1-yl-quinolin-7-ol, product of example 100, with 4-bromomethyl benzonitrile whereby the product was isolated as free base, 4-(6-fluoro-2-methyl-4-pyrrolidin-1-yl-quinolin-7-yloxymethyl)-benzonitrile as an off-white solid. ISP mass spectrum, m/e: 362.2 (M+1 calculated for $C_{22}H_{20}FN_3O$: 362).

Example 102

In analogy to example 6 there was prepared: on reaction of 6-fluoro-2-methyl-4-pyrrolidin-1-yl-quinolin-7-ol, product of example 100, with 3-bromomethyl pyridine hydrochloride whereby the product was isolated as free base, 6-fuoro-2-methyl-7-(pyridin-3-ylmethoxy)-4-pyrrolidin-1-yl-quinoline as an brown solid. ISP mass spectrum, m/e: 338.2(M+1 calculated for $C_{20}H_{20}FN_3O$: 338).

Example 103

In analogy to example 6 there was prepared: on reaction of 6-fluoro-2-methyl-4-pyrrolidin-1-yl-quinolin-7-ol, product of example 100, with 3-chloromethyl 2-fluoro-pyridine hydrochloride whereby the product was isolated as free base, 6-fluoro-7-(2-fluoro-pyridin-3-ylmethoxy)-2-methyl-4-pyrrolidin-1-yl-quinoline as an brown solid. ISP mass spectrum, m/e: 356.4 (M+1 calculated for $C_{20}H_{19}F_2N_3O$: 356).

Example 104

In analogy to example 6 there was prepared: on reaction of 6-fluoro-2-methyl-4-pyrrolidin-1-yl-quinolin-7-ol, product of example 100, with 2-chloro-3-chloromethyl-pyridine hydrochloride whereby the product was isolated as free base, 7-(2-chloro-pyridin-3-ylmethoxy)-6-fluoro-2-methyl-4-pyrrolidin-1-yl-quinoline as a light brown solid. ISP mass spectrum, m/e: 372.3 (M+1 calculated for $C_{20}H_{19}ClFN_3O$: 372).

Example 105

In analogy to example 6 there was prepared: on reaction of 6-fluoro-2-methyl-4-pyrrolidin-1-yl-quinolin-7-ol, product of example 100, with 3-chloromethyl-2-methyl-pyridine hydrochloride whereby the product was isolated as free base, 6-fluoro-2-methyl-7-(2-methyl-pyridin-3-ylmethoxy)-4-pyrrolidin-1-yl-quinoline an light yellow solid. ISP mass spectrum, m/e: 352.4(M+1 calculated for $C_{21}H_{22}FN_3O$: 352).

Example 106

In analogy to example 6 there was prepared: on reaction of 6-fluoro-2-methyl-4-pyrrolidin-1-yl-quinolin-7-ol, product of example 100, with 3-chloromethyl benzonitrile whereby the product was isolated as free base, 3-(6-fluoro-2-methyl-4-pyrrolidin-1-yl-quinolin-7-yloxymethyl)-benzonitrile as an off-white solid. ISP mass spectrum, m/e: 362.2(M+1 calculated for $C_{22}H_{20}FN_3O$: 362).

Example 107

In analogy to example 6 there was prepared: on reaction of 6-fluoro-2-methyl-4-pyrrolidin-1-yl-quinolin-7-ol, product of example 100, with 2-bromomethyl benzonitrile whereby the product was isolated as free base, 2-(6-fluoro-2-methyl-4-pyrrolidin-1-yl-quinolin-7-yloxymethyl)-benzonitrile as light brown solid. ISP mass spectrum, m/e: 362.2(M+1 calculated for $C_{22}H_{20}FN_3O$: 362).

Example 108

In analogy to example 6 there was prepared: on reaction of 6-fluoro-2-methyl-4-pyrrolidin-1-yl-quinolin-7-ol, product of example 100, with cyclopropylmethyl bromide, 7-cyclopropylmethoxy-6-fluoro-2-methyl-4-pyrrolidin-1-yl-quinoline hydrochloride as a yellow solid. ISP mass spectrum, m/e: 301.3(M+1 calculated for $C_{18}H_{21}FN_2O$: 301).

Example 109

In analogy to example 6 there was prepared: on reaction of 6-fluoro-2-methyl-4-pyrrolidin-1-yl-quinolin-7-ol, product of example 100, with 5-chloromethyl-pyridine-2-carbonitrile, whereby the product was isolated as free base, 5-(6-fluoro-2-methyl-4-pyrrolidin-1-yl-quinolin-7-yloxymethyl)-pyridine-2-carbonitrile as light grey solid. ISP mass spectrum, m/e: 363.2(M+1 calculated for $C_{21}H_{19}FN_4O$: 363).

Example 110

A suspension of 3.2 g (9.5 mmol) of (R)-1-(7-benzyloxy-2-methyl-quinolin-4-yl)-pyrrolidin-3-ol, product of example 86, in THF (275 ml) was treated at RT under nitrogen with 1.42 g (12.4 mmol) of potassium tert-butoxide. The suspension was stirred for 20 minutes at RT then 0.72 ml (11.4 mmol) of methyl iodide were added. After 25 minutes of stirring further 0.284 g (2.48 mmol) of potassium tert-butoxide were added followed by 0.144 ml (2.28 mol) of methyl iodide (10 minutes later) for completion of the reaction. Stirring was continued for 20 minutes, the reaction mixture was then concentrated in vacuo and the residue partitioned between water and AcOEt. The layers were separated the aqueous layer once extracted with AcOEt, the combined organic layers washed with brine, dried over magnesium sulphate and concentrated in vacuo to give 3.33 g (94.5%) (R)-7-benzyloxy-4-(3-methoxy-pyrrolidin-1-yl)-2-methyl-quinoline as an orange viscous oil. ISP mass spectrum, m/e: 349.5 (M+1 calculated for $C_{22}H_{24}FN_2O2$: 349).

Example 111

In analogy to example 110 there was prepared: on reaction of (S)-1-(7-benzyloxy-2-methyl-quinolin-4-yl)-pyrrolidin-3-ol, product of example 85, with 2-bromoethyl methyl ether, (S)-7-benzyloxy-4-[3-(2-methoxy-ethoxy)-pyrrolidin-1-yl]-2-methyl-quinoline an orange viscous oil. ISP mass spectrum, m/e: 393.4 (M+1 calculated for $C_{24}H_{28}N_2O_3$: 393).

Example 112

In analogy to example 110 there was prepared: on reaction of(S)-1-(7-benzyloxy-2-methyl-quinolin-4-yl)-pyrrolidin-3-ol, product of example 85, with methyl iodide, (S)-7-benzyloxy-4-(3-methoxy-pyrrolidin-1-yl)-2-methyl-quinoline as an yellow viscous oil. ISP mass spectrum, m/e: 349.3 (M+1 calculated for $C_{22}H_{24}N_2O_2$: 349).

Example 113

In analogy to example 110 there was prepared: on reaction of (S)-1-(7-benzyloxy-2-methyl-quinolin-4-yl)-pyrrolidin-3-ol, product of example 85, with cyclopropyl bromide, (S)-7-benzyloxy-4-(3-cyclopropylmethoxy-pyrrolidin-1-yl)-2-methyl-quinoline as an orange viscous oil. ISP mass spectrum, m/e: 389.2 (M+1 calculated for $C_{25}H_{28}N_2O_2$: 389).

Example 114

In analogy to example 110 there was prepared: on reaction of (S)-1-(7-benzyloxy-2-methyl-quinolin-4-yl)-pyrrolidin-3-ol, product of example 85, with toluene-4-sulfonic acid 3-methoxy-propyl ester, (S)-7-benzyloxy-4-[3-(3-methoxy-propoxy)-pyrrolidin-1-yl]-2-methyl-quinoline as an yellow viscous oil. ISP mass spectrum, m/e: 407.3 (M+1 calculated for $C_{25}H_{30}N_2O_3$: 407).

Example 115

In analogy to example 110 there was prepared: on reaction of (S)-1-(7-benzyloxy-2-methyl-quinolin-4-yl)-pyrrolidin-3-ol, product of example 85, with 2-(2-bromo-ethoxy)-tetrahydro-pyran, 7-benzyloxy-2-methyl-4-{(3S)-3-[2-(tetrahydro-pyran-2-yloxy)-ethoxy]-pyrrolidin-1-yl}-quinoline as an yellow viscous oil. ISP mass spectrum, m/e: 363.4 (M+1 calculated for $C_{28}H_{34}N_2O_4$: 463).

Example 116

In analogy to example 2, on hydrogenation of (S)-7-benzyloxy-4-[3-(2-methoxy-ethoxy)-pyrrolidin-1-yl]-2-methyl-quinoline, product of example 111, with Pd on charcoal (10%) in MeOH, there was obtained: (S)-4-[3-(2-methoxy-ethoxy)-pyrrolidin-1-yl]-2-methyl-quinolin-7-ol as a yellow solid. ISP mass spectrum, m/e: 303.4 (M+1 calculated for $C_{17}H_{22}N_2O_3$: 303).

Example 117

In analogy to example 2, on hydrogenation of (S)-7-benzyloxy-4-(3-methoxy-pyrrolidin-1-yl)-2-methyl-quinoline, product of example 112, with Pd on charcoal (10%) in MeOH, there was obtained: (S)-4-(3-methoxy-pyrrolidin-1-yl)-2-methyl-quinolin-7-ol as a yellow solid. ISP mass spectrum, m/e: 259.2 (M+1 calculated for $C_{15}H_{18}N_2O_2$: 259).

Example 118

In analogy to example 2, on hydrogenation of (S)-7-benzyloxy-4-(3-cyclopropylmethoxy-pyrrolidin-1-yl)-2-methyl-quinoline, product of example 113, with Pd on charcoal (10%) in MeOH, there was obtained: (S)-4-(3-cyclopropylmethoxy-pyrrolidin-1-yl)-2-methyl-quinolin-7-ol as a yellow solid. ISP mass spectrum, m/e: 299.3 (M+1 calculated for $C_{18}H_{22}N_2O_2$: 299).

Example 119

In analogy to example 2, on hydrogenation of (S)-7-benzyloxy-4-[3-(3-methoxy-propoxy)-pyrrolidin-1-yl]-2-methyl-quinoline, product of example 114, with Pd on charcoal (10%) in MeOH, there was obtained: (S)-4-[3-(3-methoxy-propoxy)-pyrrolidin-1-yl]-2-methyl-quinolin-7-ol as a yellow solid. ISP mass spectrum, m/e: 317 (M+1 calculated for $C_{18}H_{24}N_2O_3$: 317).

Example 120

In analogy to example 2, on hydrogenation of 7-benzyloxy-2-methyl-4-{(3S)-3-[2-(tetrahydro-pyran-2-yloxy)-ethoxy]-pyrrolidin-1-yl}-quinoline, product of example 115, with Pd on charcoal (10%) in MeOH, there was obtained: 2-methyl-4-{(3S)-3-[2-(tetrahydro-pyran-2-yloxy)-ethoxy]-pyrrolidin-1-yl}-quinolin-7-ol as a yellow solid. ISP mass spectrum, m/e: 373.4.3 (M+1 calculated for $C_{21}H_{28}N_2O_4$: 373).

Example 121

In analogy to example 6, on reaction of (S)-4-[3-(2-methoxy-ethoxy)-pyrrolidin-1-yl]-2-methyl-quinolin-7-ol, product of example 116, with 4-bromomethyl benzonitrile there was obtained: (S)-4-{4-[3-(2-methoxy-ethoxy)-pyrrolidin-1-yl]-2-methyl-quinolin-7-yloxymethyl}-benzonitrile hydrochloride as a light yellow solid. ISP mass spectrum, m/e: 418.4 (M+1 calculated for $C_{25}H_{27}N_3O_3$: 418.4).

Example 122

In analogy to example 6, on reaction of (S)-4-(3-methoxy-pyrrolidin-1-yl)-2-methyl-quinolin-7-ol, product of example 117, with 4-bromomethyl benzonitrile there was obtained: (S)-4-[4-(3-methoxy-pyrrolidin-1-yl)-2-methyl-quinolin-7-yloxymethyl]-benzonitrile hydrochloride as a light yellow solid. ISP mass spectrum, m/e: 374.4 (M+1 calculated for $C_{23}H_{23}N_3O_2$: 374).

Example 123

In analogy to example 6, on reaction of (S)-4-(3-cyclopropylmethoxy-pyrrolidin-1-yl)-2-methyl-quinolin-7-ol, product of example 118, with 4-bromomethyl benzonitrile there was obtained: (S)-4-[4-(3-cyclopropylmethoxypyrrolidin-1-yl)-2-methyl-quinolin-7-yloxymethyl]-benzonitrile hydrochloride as an off-white solid. ISP mass spectrum, m/e: 414.4 (M+1 calculated for $C_{26}H_{27}N_3O_2$: 414).

Example 124

In analogy to example 6, on reaction of (S)-4-[3-(3-methoxy-propoxy)-pyrrolidin-1-yl]-2-methyl-quinolin-7-ol, product of example 119, with 4-bromomethyl benzonitrile there was obtained: (S)-4-{4-[3-(3-methoxy-propoxy)-pyrrolidin-1-yl]-2-methyl-quinolin-7-yloxymethyl}-benzonitrile hydrochloride as an off-white solid. ISP mass spectrum, m/e: 432.5 (M+1 calculated for $C_{26}H_{29}N_3O_3$: 432).

Example 125

In analogy to example 6, on reaction of 2-methyl-4-{(3S)-3-[2-(tetrahydro-pyran-2-yloxy)-ethoxy]-pyrrolidin-1-yl}-quinolin-7-ol, product of example 120, with 4-bromomethyl benzonitrile, and subsequent cleavage of the THP ether protecting group whereby the product was isolated as free base, there was obtained: (S)-4-{4-[3-(2-Hydroxy-ethoxy)-pyrrolidin-1-yl]-2-methyl-quinolin-7-yloxymethyl}-benzonitrile as a white yellow solid. ISP mass spectrum, m/e: 405.3 (M+1 calculated for $C_{24}H_{25}N_3O_3$: 403).

Example 126

In analogy to example 99, on reaction of 7-benzyloxy-4-chloro-6-fluoro-2-methyl-quinoline, with an excess of (S)-2-(hydroxymethyl)pyrrolidine (2,5 mole-equivalents) in 1-methyl-2-pyrrolidone as solvent at 100° C., there was obtained: (S)-[1-(7-benzyloxy-6-fluoro-2-methyl-quinolin-4-yl)-pyrrolidin-2-yl]-methanol as an light brown solid. ISP mass spectrum, m/e: 367.3 (M+1 calculated for $C_{22}H_{23}FN_2O_2$: 367).

Example 127

In analogy to example 100, on hydrogenation of (S)-[1-(7-benzyloxy-6-fluoro-2-methyl-quinolin-4-yl)-pyrrolidin-2-yl]-methanol, product of example 126, with Pd on charcoal (10%) in MeOH, there was obtained: (S)-6-fluoro-4-(2-hydroxymethyl-pyrrolidin-1-yl)-2-methyl-quinolin-7-ol as a light brown solid. ISP mass spectrum, m/e: 277.3 (M+1 calculated for $C_{15}H_{17}FN_2O_2$: 277).

Example 128

In analogy to example 6, on reaction of (S)-6-fluoro-4-(2-hydroxymethyl-pyrrolidin-1-yl)-2-methyl-quinolin-7-ol, product of example 127, with 4-bromomethyl benzonitrile, whereby the product was isolated as free base, there was obtained: (S)-4-[6-fluoro-4-(2-hydroxymethyl-pyrrolidin-1-yl)-2-methyl-quinolin-7-yloxymethyl]-benzonitrile as an light grey solid. ISP mass spectrum, m/e: 392.3 (M+1 calculated for $C_{23}H_{22}FN_3O_2$: 392).

Example 129

In analogy to example 6, on reaction of (S)-6-fluoro-4-(2-hydroxymethyl-pyrrolidin-1-yl)-2-methyl-quinolin-7-ol, product of example 127, with 5-chloromethyl-pyridine-2-carbonitrile, whereby the product was isolated as free base, there was obtained: (S)-5-[6-fluoro-4-(2-hydroxymethyl-pyrrolidin-1-yl)-2-methyl-quinolin-7-yloxymethyl]-pyridine-2-carbonitrile as a grey solid. ISP mass spectrum, m/e: 393.3 (M+1 calculated for $C_{22}H_{21}FN_4O_2$: 393).

Example 130 a) A solution of 1.42 g of (4.6 mmol) of 4-(4-chloro-2-methyl-quinolin-7-yloxymethyl)-benzonitrile and 1.11 g (12.5 mmol) of (S)-3-hydroxypyrrolidine in 1-methyl-2-pyrrolidine (25 ml) was heated under nitrogen at 100° C. (oil bath temperature) for 23 h. The reaction mixture was concentrated in a high vacuum, the residue taken up in methylene chloride, which was washed with water, saturated NaCl solution and then dried over magnesium sulphate. The solvent was removed in vacuo, the residue triturated with MeOH, filtered off by suction, washed subsequently with MeOH and ether and then dried in a high vaccum to give 1.45 g (83.86%) of the (S)-4-[4-(3-hydroxy-pyrrolidin-1-yl)-2-methyl-quinolin-7-yloxymethyl]-benzonitrile as a brown solid. ISP mass spectrum, m/e: 360.2 (M+1 calculated for $C_{22}H_{21}N_3O_2$: 360.2).

Preparation of the Starting Material:

b) A solution of 3 g (10.5 mmol) of 7-benzyloxy-2-methyl-quinolin-4-ol, product of example 1 c), dissolved in 270 ml of MeOH was treated with 1 g of palladium on charcoal (10%) and then hydrogenated at RT for 1 h until HPLC analysis indicated the completion of the reaction. The catalyst was filtered off, washed with MeOH, and the solution was concentrated in vacuo. The residue was triturated with ether, collected by filtration and dried in a high vacuum to give 2.05 g (98.6%) 2-methyl-quinoline-4,7-diol as an off-white solid. ISP mass spectrum, m/e: 176.2 (M+1 calculated for $C_{10}H_9NO_2$: 176).

c) A mixture of 2.05 g (10.4 mmol) of 2-methyl-quinoline-4,7-diol, 1.72 g (12.5 mmol) of potassium carbonate and 2.1 g (12.5 mmol) of 4-(bromomethyl)-benzonitrile in 100 ml of DMF were stirred at RT under an nitrogen atmosphere for 4 h until completion of the reaction according to HPLC analysis. The reaction mixture was cooled to RT and poured into EtOAc/water (300 ml/400 ml). The product that precipitated was filtered off by suction, washed with water, AcOEt and ether and dried in a high vacuum to give 2.23 g (73%) of 4-(4-hydroxy-2-methyl-quinolin-7-yloxymethyl)-benzonitrile as a white solid. ISP mass spectrum, m/e: 291.4 (M+1 calculated for $C_{18}H_{14}N_2O_2$: 291).

d) 2.22 g (7.6 mmol) of 4-(4-hydroxy-2-methyl-quinolin-7-yloxymethyl)-benzonitrile in 14.2 ml (151.7 mmol) of $POCl_3$ were heated at 130° C. (oil bath temperature) for 1 h 50 min until completion of the reaction according to TLC analysis. The reaction mixture was cooled to RT and the solvent was removed in vacuo. The residue was taken up in ice water and stirred for 15 minutes. The pH was adjusted to values between pH 9–10 with concentrated $NH_4OH$ an stirring was continued for 2 h. The brown solid, which precipitated was filtered off by suction, washed with water and subsequently dried in a high vacuum. This gave 2.38 g (100%) of 4-(4-chloro-2-methyl-quinolin-7-yloxymethyl)-benzonitrile as a yellow solid. ISP mass spectrum, m/e: 209 (M+1 calculated for $C_{18}H_{13}ClN_2O$: 309).

Example 131

In analogy to example 130, on reaction of 4-(4-chloro-2-methyl-quinolin-7-yloxymethyl)-benzonitrile, product of example 130 d), with (R)-3-hydroxypyrrolidine, there was obtained: (R)-4-[4-(3-hydroxy-pyrrolidin-1-yl)-2-methyl-quinolin-7-yloxymethyl]-benzonitrile as a brown solid. ISP mass spectrum, m/e: 360.3 (M+1 calculated for $C_{21}H_{21}N_3O_2$: 360).

Example 132

In analogy to example 130, on reaction of 4-(4-chloro-2-methyl-quinolin-7-yloxymethyl)-benzonitrile, product of example 130 d), with (R,S)-2-methylpyrrolidine, there was obtained: (R,S)-4-[2-methyl-4-(2-methyl-pyrrolidin-1-yl)-quinolin-7-yloxymethyl]-benzonitrile as a beige solid. ISP mass spectrum, m/e: 358.2 (M+1 calculated for $C_{23}H_{23}N_3O$: 358).

Example 133

In analogy to example 130, on reaction of 4-(4-chloro-2-methyl-quinolin-7-yloxymethyl)-benzonitrile, product of example 130 d), with (S)-2-(hydroxymethyl)pyrrolidine, there was obtained: (S)-4-[4-(2-hydroxymethyl-pyrrolidin-1-yl)-2-methyl-quinolin-7-yloxymethyl]-benzonitrile as a light yellow solid. ISP mass spectrum, m/e: 374.4 (M+1 calculated for $C_{23}H_{23}N_3O2$: 374).

Example 134

In analogy to example 130, on reaction of 4-(4-chloro-2-methyl-quinolin-7-yloxymethyl)-benzonitrile, product of example 130 d), with (R)-2-(hydroxymethyl)pyrrolidine, there was obtained: (R)-4-[4-(2-hydroxymethyl-pyrrolidin-1-yl)-2-methyl-quinolin-7-yloxymethyl]-benzonitrile as a light yellow solid. ISP mass spectrum, m/e: 374.4 (M+1 calculated for $C_{23}H_{23}N_3O_2$: 374).

Example 135

In analogy to example 130, on reaction of 4-(4-chloro-2-methyl-quinolin-7-yloxymethyl)-benzonitrile, product of example 130 d), with (R)-3-(dimethylamino)pyrrolidine, there was obtained: (R)-4-[4-(3-dimethylamino-pyrrolidin-1-yl)-2-methyl-quinolin-7-yloxymethyl]-benzonitrile as a light brown solid. ISP mass spectrum, m/e: 387.3 (M+1 calculated for $C_{24}H_{26}N_4O$: 387).

Example 136

In analogy to example 130, on reaction of 4-(4-chloro-2-methyl-quinolin-7-yloxymethyl)-benzonitrile, product of example 130 d), with (S)-3-(dimethylamino)pyrrolidine, there was obtained: (S)-4-[4-(3-dimethylamino-pyrrolidin-1-yl)-2-methyl-quinolin-7-yloxymethyl]-benzonitrile as a light brown solid. ISP mass spectrum, m/e: 387.3 (M+1 calculated for $C_{24}H_{26}N_4O$: 387).

Example 137

In analogy to example 130, on reaction of 4-(4-chloro-2-methyl-quinolin-7-yloxymethyl)-benzonitrile, product of example 130 d), with (R)-2-(methoxymethyl)pyrrolidine, there was obtained: (R)-4-[4-(2-methoxymethyl-pyrrolidin-1-yl)-2-methyl-quinolin-7-yloxymethyl]-benzonitrile as a light brown solid. ISP mass spectrum, m/e: 388.3 (M+1 calculated for $C_{24}H_{25}N_3O_2$: 388).

Example 138

In analogy to example 130, on reaction of 4-(4-chloro-2-methyl-quinolin-7-yloxymethyl)-benzonitrile, product of example 130 d), with (S)-2-(methoxymethyl)pyrrolidine, there was obtained: (S)-4-[4-(2-methoxymethyl-pyrrolidin-1-yl)-2-methyl-quinolin-7-yloxymethyl]-benzonitrile as a light brown solid. ISP mass spectrum, m/e: 388.3 (M+1 calculated for $C_{24}H_{25}N_3O_2$: 388).

Example 139

In analogy to example 130, on reaction of 4-(4-chloro-2-methyl-quinolin-7-yloxymethyl)-benzonitrile, product of example 130 d), with (R,S)-2-isopropyl-pyrrolidine, there was obtained: (R,S)-4-[4-(2-isopropyl-pyrrolidin-1-yl)-2-methyl-quinolin-7-yloxymethyl]-benzonitrile hydrochloride as a light yellow solid. ISP mass spectrum, m/e: 386.4 (M+1 calculated for $C_{25}H_{27}N_3O$: 386).

Example 140

In analogy to example 130, on reaction of 4-(4-chloro-2-methyl-quinolin-7-yloxymethyl)-benzonitrile, product of example 130 d), with (S)-proline methyl ester, there was obtained: (S)-1-[7-(4-cyano-benzyloxy)-2-methyl-quinolin-4-yl]-pyrrolidine-2-carboxylic acid methyl ester as a white solid. ISP mass spectrum, m/e: 402.5 (M+1 calculated for $C_{24}H_{23}N_3O_3$: 402).

Example 141

In analogy to example 130, on reaction of 4-(4-chloro-2-methyl-quinolin-7-yloxymethyl)-benzonitrile, product of example 130 d), with (R)-3-(methylamino)pyrrolidine there was obtained: (R)-4-[2-methyl-4-(3-methylamino-pyrrolidin-1-yl)-quinolin-7-yloxymethyl]-benzonitrile as a yellow foam. ISP mass spectrum, m/e: 373.4 (M+1 calculated for $C_{23}H_{24}N_4O$: 373).

Example 142

In analogy to example 130, on reaction of 4-(4-chloro-2-methyl-quinolin-7-yloxymethyl)-benzonitrile, product of example 130 d), with (S)-3-(methylamino)pyrrolidine there was obtained: (S)-4-[2-methyl-4-(3-methylamino-pyrrolidin-1-yl)-quinolin-7-yloxymethyl]-benzonitrile as a brown foam. ISP mass spectrum, m/e: 373.4 (M+1 calculated for $C_{23}H_{24}N_4O$: 373).

Example 143

In analogy to example 130, on reaction of 4-(4-chloro-2-methyl-quinolin-7-yloxymethyl)-benzonitrile, product of example 130 d), with piperidine there was obtained: 4-(2-methyl-4-piperidin-1-yl-quinolin-7-yloxymethyl)-benzonitrile hydrochloride as a yellow solid. ISP mass spectrum, m/e: 358.3 (M+1 calculated for $C_{23}H_{23}N_3O$: 358).

Example 144

In analogy to example 130, on reaction of 4-(4-chloro-2-methyl-quinolin-7-yloxymethyl)-benzonitrile, product of example 130 d), with morpholine there was obtained: 4-(2-methyl-4-morpholin-4-yl-quinolin-7-yloxymethyl)-benzonitrile hydrochloride as a light yellow solid. ISP mass spectrum, m/e: 360.3 (M+1 calculated for $C_{22}H_{21}N_3O_2$: 360).

Example 145

In analogy to example 130, on reaction of 4-(4-chloro-2-methyl-quinolin-7-yloxymethyl)-benzonitrile, product of example 130 d), with (R,S)-3-(diethylamino)pyrrolidine there was obtained: (R,S)-4-[4-(3-diethylamino-pyrrolidin-1-yl)-2-methyl-quinolin-7-yloxymethyl]-benzonitrile hydrochloride as a light brown solid. ISP mass spectrum, m/e: 415.4 (M+1 calculated for $C_{22}H_{21}N_3O_2$: 415).

Example 146

In analogy to example 130, on reaction of 4-(4-chloro-2-methyl-quinolin-7-yloxymethyl)-benzonitrile, product of example 130 d), with (R,S)-2-(pyrrolidin-3yl)-pyridine there was obtained: (R,S)-4-[2-methyl-4-(3-pyridin-2-yl-pyrrolidin-1-yl)-quinolin-7-yloxymethyl]-benzonitrile

Example 147

In analogy to example 130, on reaction of 4-(4-chloro-2-methyl-quinolin-7-yloxymethyl)-benzonitrile, product of example 130 d), with (R,S)-4-(pyrrolidin-3-yl)-pyridine there was obtained: (R,S)-4-[2-methyl-4-(3-pyridin-4-yl-pyrrolidin-1-yl)-quinolin-7-yloxymethyl]-benzonitrile as a white solid. ISP mass spectrum, m/e: 421.4 (M+1 calculated for $C_{27}H_{24}N_4O$: 421).

Example 148

In analogy to example 130, on reaction of 4-(4-chloro-2-methyl-quinolin-7-yloxymethyl)-benzonitrile, product of example 130 d), with (S)-1-(2-pyrrolidinylmethyl)pyrrolidine there was obtained: (S)-4-[2-methyl-4-(2-pyrrolidin-1-ylmethyl-pyrrolidin-1-yl)-quinolin-7-yloxymethyl]-benzonitrile hydrochloride as a brown solid. ISP mass spectrum, m/e: 427.6 (M+1 calculated for $C_{27}H_{30}N_4O$: 427).

Example 149

In analogy to example 130, on reaction of 4-(4-chloro-2-methyl-quinolin-7-yloxymethyl)-benzonitrile, product of example 130 d), with (R,S)-3-(methylsulfonyl)-pyrrolidine there was obtained: (R,S)-4-[4-(3-methanesulfonyl-pyrrolidin-1-yl)-2-methyl-quinolin-7-yloxymethyl]-benzonitrile hydrochloride as a light brown solid. ISP mass spectrum, m/e: 422.4 (M+1 calculated for $C_{23}H_{23}N_3O_3S$: 422).

Example 150

In analogy to example 130, on reaction of 4-(4-chloro-2-methyl-quinolin-7-yloxymethyl)-benzonitrile, product of example 130 d), with (R,S)-3-methyl-piperidine there was obtained: (R,S)-4-[2-methyl-4-(3-methyl-piperidin-1-yl)-quinolin-7-yloxymethyl]-benzonitrile hydrochloride as a light yellow solid. ISP mass spectrum, m/e: 372.4 (M+1 calculated for $C_{24}H_{25}N_3O$: 372).

Example 151

In analogy to example 130, on reaction of 4-(4-chloro-2-methyl-quinolin-7-yloxymethyl)-benzonitrile, product of example 130 d), with 1,4-dioxa-8-azaspiro{4.5}decane there was obtained: 4-[4-(1,4-dioxa-8-aza-spiro[4.5]dec-8-yl)-2-methyl-quinolin-7-yloxymethyl]-benzonitrile as a light yellow solid. ISP mass spectrum, m/e: 416.4 (M+1 calculated for $C_{25}H_{25}N_3O_3$: 416).

Example 152

In analogy to example 130, on reaction of 4-(4-chloro-2-methyl-quinolin-7-yloxymethyl)-benzonitrile, product of example 130 d), with (R,S)-3-(hydroxymethyl)piperidine there was obtained: (R,S)-4-[4-(3-hydroxymethyl-piperidin-1-yl)-2-methyl-quinolin-7-yloxymethyl]-benzonitrile as a light yellow solid. ISP mass spectrum, m/e: 388.3 (M+1 calculated for $C_{24}H_{25}N_3O_2$: 388).

Example A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Upon reading the present specification various embodiments will become obvious to the skilled artisan. These variations are to be considered within the scope and spirit of the present invention which is only to be limited by the claims that follow and their equivalents.

What is claimed is:

1. A compound of formula:

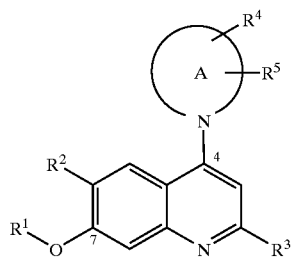

wherein:

$R^1$ is hydrogen, alkyl, alkoxyalkyl, alkenyl, alkinyl, hydroxyalkyl, aralkyl, heterocyclylalkyl, cycloalkylalkyl, $NH_2$—$SO_2$—, monoalkylamino-$SO_2$—, dialkylamino-$SO_2$—, alkyl-$SO_2$—, aryl, $NH_2$-alkyl, monoalkylaminoalkyl, dialkylaminoalkyl, alkoxycarbonylalkyl, carboxyalkyl, aryl-$SO_2$—O-alkyl, cycloalkyl, or cycloalkylalkyl;

$R^2$ is hydrogen, halogen, alkyl, alkenyl, alkinyl, aralkyl, heteroarylalkyl, hydroxyalkyl, alkoxy, alkoxyalkoxy, hydroxyalkoxyalkyl, aryloxy, arylamino, heteroarylamino, $NH_2$—, monoalkylamino, dialkylamino, heterocyclyl, arylalkylamino, heteroarylalkylamino, aryl, arylalkoxy, or heteroarylalkoxy;

$R^3$ is alkyl;

$R^4$ is hydrogen, alkyl, cycloalkyl, alkoxy, hydroxy, $NH_2$—, monoalkylamino, dialkylamino, acetylamino, cyano, hydroxyalkyl, alkoxyalkyl, cycloalkoxy, alkoxyalkoxy, cycloalkylalkoxy, heterocyclyl, heterocyclyloxy, heterocyclyloxyalkoxy, hydroxyalkoxy, alkoxycarbonyl, carboxy, heterocyclylalkyl, alkyl-SO$_2$—, or aryl-SO$_2$—;

R$^5$ is hydrogen, alkyl, cycloalkyl, alkoxy, hydroxy, NH$_2$—, monoalkylamino, dialkylamino, acetylamino, cyano, hydroxyalkyl, alkoxyalkyl, cycloalkoxy, alkoxyalkoxy, cycloalkylalkoxy, heterocyclyl, heterocyclyloxy, heterocyclyloxyalkoxy, hydroxyalkoxy, alkoxycarbonyl, carboxy, heterocyclylalkyl, alkyl-SO$_2$—, or aryl-SO$_2$—;

A is pyrrolidinyl;

or a pharmaceutically acceptable salt or ester thereof.

2. The compound according to claim 1, wherein

R$^1$ is hydrogen, alkyl, alkoxyalkyl, alkenyl, alkinyl, hydroxyalkyl, aralkyl, heterocyclylalkyl, cycloalkylalkyl, NH$_2$—SO$_2$—, monoalkylamino-SO$_2$—, dialkylamino-SO$_2$—, or alkyl-SO$_2$—;

R$^4$ is hydrogen, alkyl, alkoxy, hydroxy, NH$_2$—, monoalkylamino, dialkylamino, acetylamino, or cyano; and R$^5$ is hydrogen.

3. The compound according to claim 1, wherein R$^1$ is hydrogen, cycloalkylalkyl, aralkyl, or heteroarylalkyl.

4. The compound according to claim 3, wherein R$^1$ is hydrogen, aralkyl or heteroarylalkyl.

5. The compound according to claim 4, wherein R$^1$ is hydrogen, phenylalkyl, pyridinylalkyl, phenylalkyl wherein the phenyl cycle is substituted by one to three substituents independently selected from the group consisting of alkoxy, cyano and halogen, and pyridinylalkyl wherein the pyridinyl cycle is substituted by one to three substituents independently selected from the group consisting of alkoxy, cyano and halogen.

6. The compound according to claim 5, wherein R$^1$ is hydrogen, cyclopropylmethyl, (methoxyphenyl)methyl, (cyanophenyl)methyl, (chlorophenyl)methyl, pyridinylmethyl, chloropyridinylmethyl, or fluoropyridinylmethyl.

7. The compound according to claim 1, wherein R$^2$ is hydrogen, alkyl or halogen.

8. The compound according to claim 7, wherein R$^2$ is hydrogen.

9. The compound according to claim 7, wherein R$^2$ is alkyl.

10. The compounds according to claim 7, wherein R$^2$ is hydrogen, butyl, fluoro, chloro or bromo.

11. The compound according to claim 1, wherein R$^3$ is methyl.

12. The compound according to claim 1, wherein R$^4$ is hydrogen, alkoxy, alkoxyalkyl, hydroxyalkyl or hydroxy.

13. The compound according to claim 12, wherein R$^4$ is hydrogen.

14. The compound according to claim 1, wherein R$^5$ is hydrogen.

15. A compound of formula:

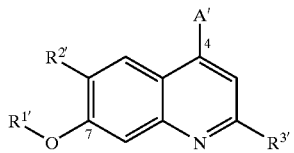

I' wherein:

R$^{1'}$ is hydrogen, phenylalkyl, pyridinylalkyl, phenylalkyl wherein the phenyl cycle is substituted by a substituent selected from the group consisting of alkoxy, cyano and halogen, and pyridinylalkyl wherein the pyridinyl cycle is substituted by a substituent selected from the group consisting of alkoxy, cyano and halogen;

R$^{2'}$ is is hydrogen, alkyl or halogen;

R$^{3'}$ is alkyl;

A' is selected from the group consisting of pyrrolidinyl and pyrrolidinyl substituted by hydroxy, alkyloxy, hydroxyalkyl or alkyloxyalkyl;

or a pharmaceutically acceptable salt or ester thereof.

16. The compound according to claim 15, wherein R$^{3'}$ is methyl.

17. The compound according to claim 15, wherein A' is pyrrolidinyl.

18. The compound according to claim 17, wherein R$^{2'}$ is alkyl.

19. The compound according to claim 18, R$^{2'}$ is butyl.

20. The compound according to claim 19, wherein R$^{1'}$ is hydrogen.

21. The compound according to claim 20 which is 6-butyl-4-pyrrolidin-1-yl-quinolin-7-ol or a pharmaceutically acceptable salt or ester thereof.

22. The compound according to claim 19, wherein R$^{1'}$ is (cyanophenyl)methyl.

23. The compound according to claim 22 which is 4-(6-butyl-4-pyrrolidin-1-yl-quinolin-7-yloxymethyl)-benzonitrile or a pharmaceutically acceptable salt or ester thereof.

24. The compound according to claim 16, wherein R$^{3'}$ is methyl.

25. The compound according to claim 24, wherein A' is pyrrolidinyl or pyrrolidinyl which is substituted by hydroxy, alkyloxy, hydroxyalkyl or alkyloxyalkyl.

26. The compound according to claim 25, wherein A' is pyrrolidinyl.

27. The compound according to claim 26, wherein R$^{2'}$ is hydrogen or halogen.

28. The compound according to claim 27, wherein R$^{2'}$ is hydrogen.

29. The compound according to claim 28, wherein R$^{1'}$ is hydrogen, phenylalkyl wherein the phenyl cycle is substituted by a substituent selected from the group consisting of alkoxy, cyano and halogen, and pyridinylalkyl wherein the pyridinyl cycle is substituted by a substituent selected from the group consisting of alkoxy, cyano and halogen.

30. The compound according to claim 29, wherein R$^{1'}$ is hydrogen.

31. The compound according to claim 30 which is 2-methyl-4-pyrrolidin-1-yl-quinolin-7-ol or a pharmaceutically acceptable salt or ester thereof.

32. The compound according to claim 29, wherein R$^{1'}$ is (methoxyphenyl)methyl.

33. The compound according to claim 32 which is 7-(3-methoxy-benzyloxy)-2-methyl-4-pyrrolidin-1-yl-quinoline or a pharmaceutically acceptable salt or ester thereof.

34. The compound according to claim 29, wherein R$^{1'}$ is (cyanophenyl)methyl.

35. The compound according to claim 34 which is 2-(2-methyl-4-pyrrolidin-1-yl-quinolin-7-yloxymethyl)-benzonitrile or a pharmaceutically acceptable salt or ester thereof.

36. The compound according to claim 34 which is 4-(2-methyl-4-pyrrolidin-1-yl-quinolin-7-yloxymethyl)-benzonitrile or a pharmaceutically acceptable salt or ester thereof.

37. The compound according to claim 29, wherein R$^{1'}$ is (chlorophenyl)methyl.

38. The compound according to claim 37 which is 7-(3-chloro-benzyloxy)-2-methyl-4-pyrrolidin-1-yl-quinoline or a pharmaceutically acceptable salt or ester thereof.

39. The compound according to claim 37 which is 7-(4-chloro-benzyloxy)-2-methyl-4-pyrrolidin-1-yl-quinoline or a pharmaceutically acceptable salt or ester thereof.

40. The compound according to claim 29, wherein $R^{1'}$ is (chloropyridinyl)methyl.

41. The compound according to claim 40 which is 7-(2-chloro-pyridin-3-ylmethoxy)-2-methyl-4-pyrrolidin-1-yl-quinoline or a pharmaceutically acceptable salt or ester thereof.

42. The compound according to claim 27, wherein $R^{2'}$ is halogen.

43. The compound according to claim 42, wherein $R^{2'}$ is fluoro.

44. The compound according to claim 43, wherein $R^{1'}$ is (cyanophenyl)methyl.

45. The compound according to claim 44 which is 4-(6-fluoro-2-methyl-4-pyrrolidin-1-yl-quinolin-7-yloxymethyl)-benzonitrile or a pharmaceutically acceptable salt or ester thereof.

46. The compound according to claim 45, wherein $R^{1'}$ is (fluoropyridinyl)methyl.

47. The compound according to claim 46 which is 6-fluoro-7-(2-fluoro-pyridin-3-ylmethoxy)-2-methyl-4-pyrrolidin-1-yl-quinoline or a pharmaceutically acceptable salt or ester thereof.

48. The compound according to claim 45, wherein $R^{1'}$ is (chloropyridinyl)methyl.

49. The compound according to claim 48 which is 7-(2-chloro-pyridin-3-ylmethoxy)-6-fluoro-2-methyl-4-pyrrolidin-1-yl-quinoline or a pharmaceutically acceptable salt or ester thereof.

50. The compound according to claim 25, wherein A' is pyrrolidinyl which is substituted by hydroxy, alkyloxy, hydroxyalkyl or alkyloxyalkyl.

51. The compound according to claim 50, wherein A' is pyrrolidinyl which is substituted by hydroxy.

52. The compound according to claim 51, wherein $R^{1'}$ is (cyanophenyl)methyl.

53. The compound according to claim 52, wherein $R^{2'}$ is hydrogen.

54. The compound according to claim 53 which is (S)-4-[4-(3-hydroxy-pyrrolidin-1-yl)-2-methyl-quinolin-7-yloxymethyl]-benzonitrile or a pharmaceutically acceptable salt or ester thereof.

55. The compound according to claim 53 which is (R)-4-[4-(3-hydroxy-pyrrolidin-1-yl)-2-methyl-quinolin-7-yloxymethyl]-benzonitrile or a pharmaceutically acceptable salt or ester thereof.

56. The compound according to claim 50, wherein A' is pyrrolidinyl which is substituted by alkyloxy.

57. The compound according to claim 56, wherein A' is pyrrolidinyl which is substituted by methoxy.

58. The compound according to claim 57, wherein $R^{1'}$ is (cyanophenyl)methyl.

59. The compound according to claim 58, which is (S)-4-[4-(3-methoxy-pyrrolidin-1-yl)-2-methyl-quinolin-7-yloxymethyl]-benzonitrile or a pharmaceutically acceptable salt or ester thereof.

60. The compound according to claim 56, wherein A' is pyrrolidinyl which is substituted by ethoxy.

61. The compound according to claim 60, wherein $R^{2'}$ is hydrogen.

62. The compound according to claim 61, wherein $R^{1'}$ is (cyanophenyl)methyl.

63. The compound according to claim 62 which is (S)-4-[4-(3-ethoxy-pyrrolidin-1-yl)-2-methyl-quinolin-7-yloxymethyl]-benzonitrile or a pharmaceutically acceptable salt or ester thereof.

64. The compound according to claim 61, wherein $R^{1'}$ is (fluoropyridinyl)methyl.

65. The compound according to claim 64 which is (S) 4-(3-ethoxy-pyrrolidin-1-yl)-7-(2-fluoro-pyridin-3-ylmethoxy)-2-methyl-quinoline or a pharmaceutically acceptable salt or ester thereof.

66. The compound according to claim 61, wherein $R^{1'}$ is (chloropyridinyl)methyl.

67. The compound according to claim 66 which is (S) 7-(2-chloro-pyridin-3-ylmethoxy)-4-(3-ethoxy-pyrrolidin-1-yl)-2-methyl-quinoline or a pharmaceutically acceptable salt or ester thereof.

68. The compound according to claim 50, wherein A' is pyrrolidinyl which is substituted by hydroxyalkyl.

69. The compound according to claim 68, wherein A' is pyrrolidinyl which is substituted by hydroxymethyl.

70. The compound according to claim 69, wherein $R^{2'}$ is hydrogen.

71. The compound according to claim 70, wherein $R^{1'}$ is (fluoropyridinyl)methyl.

72. The compound according to claim 71 which is (S)-{1-[7-(2-fluoro-pyridin-3-ylmethoxy)-2-methyl-quinolin-4-yl]-pyrrolidin-2-yl}-methanol or a pharmaceutically acceptable salt or ester thereof.

73. The compound according to claim 70, wherein $R^{1'}$ is (chloropyridinyl)methyl.

74. The compound according to claim 73 which is (S)-{1-[7-(2-chloro-pyridin-3-ylmethoxy)-2-methyl-quinolin-4-yl]-pyrrolidin-2-yl}-methanol or a pharmaceutically acceptable salt or ester thereof.

75. The compound according to claim 70, wherein $R^{1'}$ is (cyanophenyl)methyl.

76. The compound according to claim 75 which is (S)-4-[4-(2-hydroxymethyl-pyrrolidin-1-yl)-2-methyl-quinolin-7-yloxymethyl]-benzonitrile or a pharmaceutically acceptable salt or ester thereof.

77. The compound according to claim 75 which is (R)-4-[4-(2-hydroxymethyl-pyrrolidin-1-yl)-2-methyl-quinolin-7-yloxymethyl]-benzonitrile or a pharmaceutically acceptable salt or ester thereof.

78. The compound according to claim 69, wherein $R^{2'}$ is halogen.

79. The compound according to claim 78, wherein $R^{2'}$ is fluoro.

80. The compound according to claim 79, wherein $R^{1'}$ is (cyanophenyl)methyl.

81. The compound according to claim 80 which is (S)-4-[6-fluoro-4-(2-hydroxymethyl-pyrrolidin-1-yl)-2-methyl-quinolin-7-yloxymethyl]-benzonitrile or a pharmaceutically acceptable salt or ester thereof.

82. The compound according to claim 50, wherein A' is pyrrolidinyl which is substituted by alkyloxyalkyl.

83. The compound according to claim 82, wherein A' is pyrrolidinyl which is substituted by methoxymethyl.

84. The compound according to claim 83, wherein $R^{2'}$ is hydrogen.

85. The compound according to claim 84, wherein $R^{1'}$ is (fluoropyridinyl)methyl.

86. The compound according to claim 85, which is (S)-7-(2-fluoro-pyridin-3-ylmethoxy)-4-(2-methoxymethyl-pyrrolidin-1-yl)-2-methyl-quinoline or a pharmaceutically acceptable salt or ester thereof.

87. The compound according to claim 84, wherein $R^{1'}$ is (chloropyridinyl)methyl.

88. The compound according to claim 87 which is (S)-7-(2-chloro-pyridin-3-ylmethoxy)-4-(2-methoxymethyl-pyrrolidin-1-yl)-2-methyl-quinoline or a pharmaceutically acceptable salt or ester thereof.

* * * * *